(12) United States Patent
Greene et al.

(10) Patent No.: US 8,022,176 B2
(45) Date of Patent: *Sep. 20, 2011

(54) FAS PEPTIDE MIMETICS AND USES THEREOF

(75) Inventors: Mark I. Greene, Penn Valley, PA (US); Ramachandran Murali, Drexel Hill, PA (US); Akihiro Hasegawa, Chiba (JP)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 512 days.

This patent is subject to a terminal disclaimer.

(21) Appl. No.: 11/869,556

(22) Filed: Oct. 9, 2007

(65) Prior Publication Data

US 2008/0153742 A1    Jun. 26, 2008

Related U.S. Application Data

(63) Continuation of application No. 10/445,399, filed on May 23, 2003, now Pat. No. 7,288,519.

(60) Provisional application No. 60/383,309, filed on May 23, 2002, provisional application No. 60/465,943, filed on Apr. 28, 2003.

(51) Int. Cl.
*A61K 38/12* (2006.01)
(52) U.S. Cl. ...................................................... 530/317
(58) Field of Classification Search ........................ None
See application file for complete search history.

(56) References Cited

U.S. PATENT DOCUMENTS

| | | | | |
|---|---|---|---|---|
| 2,738,366 | A | * | 3/1956 | Vassel ............................ 562/445 |
| 5,632,994 | A | | 5/1997 | Reed et al. |
| 5,747,245 | A | | 5/1998 | Reed et al. |
| 6,265,535 | B1 | * | 7/2001 | Greene et al. .................. 530/317 |
| 6,548,634 | B1 | | 4/2003 | Ballinger et al. |
| 2003/0148932 | A1 | | 8/2003 | Greene et al. |

FOREIGN PATENT DOCUMENTS

| | | |
|---|---|---|
| JP | 2002-114800 | 4/2002 |
| JP | 2002-138099 | 5/2002 |
| WO | 98/53842 | 12/1998 |
| WO | WO 99/33965 A1 | 7/1999 |
| WO | 99/65935 | 1/2000 |
| WO | WO 02/66980 A1 | 8/2002 |

OTHER PUBLICATIONS

Ettmayer P. et al. J. Med. Chem. (2004) 47(10), pp. 2393-2404), prodrugs are often accidental discoveries and TESTA (B. Testa. Biochem. Pharm. (2004) 68, pp. 2393-2404.*
H.-K. Han. AAPS Pharmsci. (2000) 2(1), article 6, pp. 1-11.*
Hasegawa, Akihiro et al. "FAS-Disabling Small Exocyclic Peptide Mimetics Limit Apoptosis by an Unexpected Mechanism." Proceedings of the National Academy of Sciences of the United States of America, vol. 101, No. 17, Apr. 27, 2004; 6599-6604, XP002360129; ISSN: 0027-8424.
Park, "Rationally Designed Anti-HER2/neu Peptide Mimetic Disables P185HER2/neu Tyrosine Kinases In Vitro and In Vivo." Nat. Biotecnology, Feb. 2000, 18(2): 194-8.
Bajorath j, et al. "Analysis of fas-ligand interactions using a molecular model of the receptor-ligand interface", *J. of Computer-aided Molecular Design* 13: 1999, 409-418.
Murali et al., "Antibody Like Peptidomimetics as Large Scale Immunodetection Probes", Cell. Mol. Biol., Mar. 2003, 49(2), 209-216.

* cited by examiner

*Primary Examiner* — Cecilia J Tsang
*Assistant Examiner* — Thomas Heard
(74) *Attorney, Agent, or Firm* — Woodcock Washburn, LLP

(57) ABSTRACT

Exocyclic peptide mimetics that disable Fas were developed. A three dimensional model of the Fas receptor-ligand complex was constructed and structurally predicted regions of the receptor that were relevant to binding ligand were used to create constrained peptide mimetics. Exocyclic anti-Fas peptide mimetics were identified that block Fas receptor-ligand interactions, and modulate Fas biological activity both in vitro and in vivo. The mimetics are useful, e.g., for treating Fas-related pathologies.

14 Claims, 6 Drawing Sheets

FIG. 1A
FIG. 1B
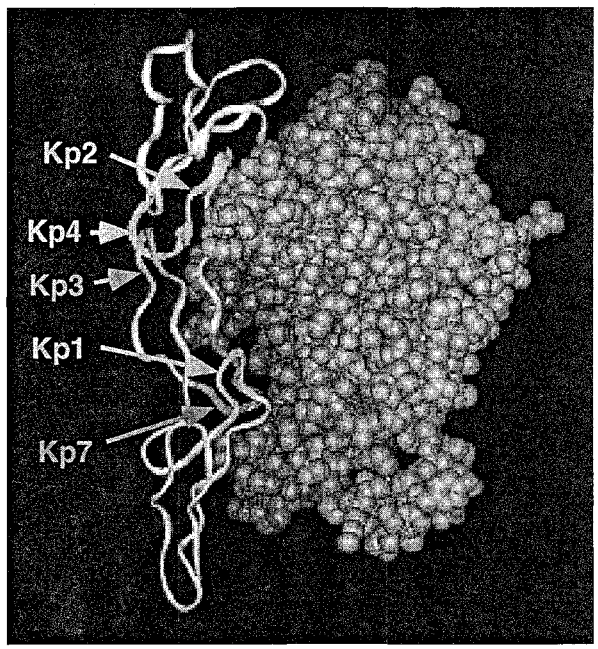
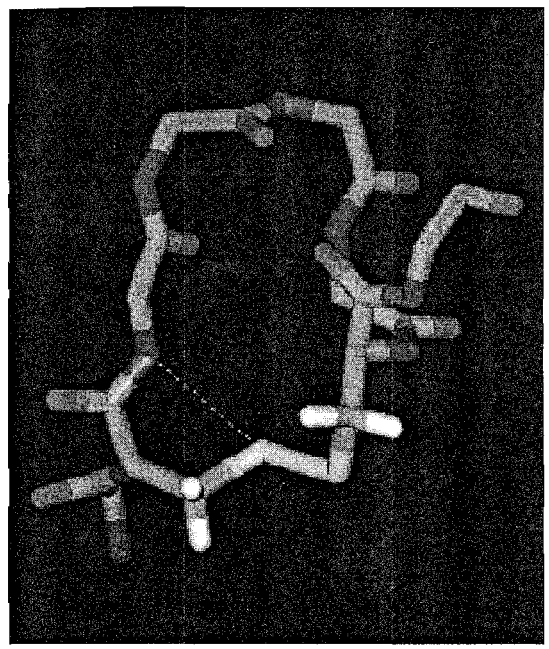

```
                    SEQUENCE LISTING

<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: Synthetic construct

<400> SEQUENCE: 1

Tyr Cys Asp Glu Gly His Leu Cys Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic construct

<400> SEQUENCE: 2

Tyr Cys Asp Glu Gly Leu Cys Tyr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Tyr Cys Asp Glu Gly Tyr Phe Cys Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic construct

<400> SEQUENCE: 4

Tyr Cys Asp Glu Gly Glu Tyr Cys Tyr
```

<210> SEQ ID NO 5
<211> LENGTH: 8
<212> TYPE: PRT
<213> ORGANISM: Artificial Sequence
<220> FEATURE:
<223> OTHER INFORMATION: Synthetic construct

<400> SEQUENCE: 5

Tyr Cys Asp Glu His Phe Cys Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Tyr Cys Asp Glu His Gly Leu Cys Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Tyr Cys Asp Glu His Gly Gln Cys Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic construct

<400> SEQUENCE: 8

Tyr Cys Asp Glu Lys Phe Cys Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic construct

<400> SEQUENCE: 9

Tyr Cys Asp Glu Gln Phe Cys Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic construct

<400> SEQUENCE: 10

Tyr Cys Asn Ser Thr Val Cys Tyr
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Tyr Cys Asp Lys Ala Glu His Phe Cys Tyr
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Synthetic construct

<400> SEQUENCE: 12

Tyr Cys Asn Thr Arg Thr Gln Asn Thr Cys Tyr
 1               5                  10

<210> SEQ ID NO 13
<211> LENGTH: 9
<212> TYPE: PRT
<213> ORGANISM: Artificial Sequence
<220> FEATURE:
<223> OTHER INFORMATION: Synthetic construct

<400> SEQUENCE: 13

Tyr Cys Gln Glu Lys Glu Tyr Cys Tyr
 1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic construct

<400> SEQUENCE: 14

Tyr Cys Gln Glu Arg Lys Glu Tyr Cys Tyr
 1               5                  10

<210> SEQ ID NO 15
<211> LENGTH: 319
<212> TYPE: PRT
<213> ORGANISM: Artificial Sequence
<220> FEATURE:
<223> OTHER INFORMATION: Synthetic construct

<400> SEQUENCE: 15

Arg Leu Ser Ser Lys Ser Val Asn Ala Gln Val Thr Asp Ile Asn Ser
 1               5                  10                  15

Lys Gly Leu Glu Leu Arg Lys Thr Val Thr Thr Val Glu Thr Gln Asn
                20                  25                  30

Leu Glu Gly Leu His His Asp Gly Gln Phe Cys His Lys Pro Cys Pro
            35                  40                  45

Pro Gly Glu Arg Lys Ala Arg Asp Cys Thr Val Asn Gly Asp Glu Pro
        50                  55                  60

Asp Cys Val Pro Cys Gln Glu Gly Lys Glu Tyr Thr Asp Lys Ala His
65                  70                  75                  80

Phe Ser Ser Lys Cys Arg Arg Cys Arg Leu Cys Asp Glu Gly His Gly
                85                  90                  95

```
Leu Glu Val Glu Ile Asn Cys Thr Arg Thr Gln Asn Thr Lys Cys Arg
                100                 105                 110

Cys Lys Pro Asn Phe Phe Cys Asn Ser Thr Val Cys Glu His Cys Asp
            115                 120                 125

Pro Cys Thr Lys Cys Glu His Gly Ile Ile Lys Glu Cys Thr Leu Thr
130             135                 140

Ser Asn Thr Lys Cys Lys Glu Glu Gly Ser Arg Ser Asn Leu Gly Trp
145                 150                 155                 160

Leu Cys Leu Leu Leu Leu Pro Ile Pro Leu Ile Val Trp Val Lys Arg
                165                 170                 175

Lys Glu Val Gln Lys Thr Cys Arg Lys His Arg Lys Glu Asn Gln Gly
            180                 185                 190

Ser His Glu Ser Pro Thr Leu Asn Pro Glu Thr Val Ala Ile Asn Leu
        195                 200                 205

Ser Asp Val Asp Leu Ser Lys Tyr Ile Thr Thr Ile Ala Gly Val Met
    210                 215                 220

Thr Leu Ser Gln Val Lys Gly Phe Val Arg Lys Asn Gly Val Asn Glu
225                 230                 235                 240

Ala Lys Ile Asp Glu Ile Lys Asn Asp Asn Val Gln Asp Thr Ala Glu
                245                 250                 255

Gln Lys Val Gln Leu Leu Arg Asn Trp His Gln Leu His Gly Lys Lys
            260                 265                 270

Glu Ala Tyr Asp Thr Leu Ile Lys Asp Leu Lys Lys Ala Asn Leu Cys
        275                 280                 285

Thr Leu Ala Glu Lys Ile Gln Thr Ile Ile Leu Lys Asp Ile Thr Ser
    290                 295                 300

Asp Ser Glu Asn Ser Asn Phe Arg Asn Glu Ile Gln Ser Leu Val
305                 310                 315

<210> SEQ ID NO 16
<211> LENGTH: 6
<212> TYPE: PRT
<213> ORGANISM: Artificial Sequence
<220> FEATURE:
<223> OTHER INFORMATION: Synthetic construct

<400> SEQUENCE: 16

Cys Asn Ser Thr Val Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic construct

<400> SEQUENCE: 17

Asp Lys Ala His Phe Ser Ser Lys Cys
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic construct

<400> SEQUENCE: 18

Cys Thr Arg Thr Gln
1               5
```

```
<210> SEQ ID NO 19
<211> LENGTH: 7
<212> TYPE: PRT
<213> ORGANISM: Artificial Sequence
<220> FEATURE:
<223> OTHER INFORMATION: Synthetic construct

<400> SEQUENCE: 19

Cys Gln Glu Gly Lys Glu Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic construct

<400> SEQUENCE: 20

Cys Asp Glu Gly His Gly Leu
1               5
```

FAS PEPTIDE MIMETICS AND USES THEREOF

CROSS-REFERENCE TO RELATED APPLICATIONS

This application is a continuation of prior patent application Ser. No. 10/445,399, filed May 23, 2003, which claims priority under 35 U.S.C. §119(e) to provisional U.S. patent application Ser. Nos. 60/383,309, filed May 23, 2002, and 60/465,943, filed Apr. 28, 2003. All of the aforesaid applications are incorporated herein by reference in their entireties.

GOVERNMENT SUPPORT

The work leading to this invention was supported at least in part by grants PO1 CA89480 and RO1 89481 awarded by the National Cancer Institute. The United States government may have certain rights to this invention pursuant to the terms of those grants.

FIELD OF THE INVENTION

The present invention relates to therapeutic agents that act by disrupting or inhibiting signaling through cell surface receptors. More specifically, the invention is directed to peptide mimetics that inhibit signaling through the Fas receptor, and to methods of using such peptide mimetics to treat Fas-related pathologies.

BACKGROUND OF THE INVENTION

Fas (CD95/APO-1) and its specific ligand (FasL/CD95L) are members of the tumor necrosis factor (TNF) receptor and TNF families of proteins, respectively. (Nagata, S. et al. *Science* 267, 1449-1456 (1995). Interaction between Fas and FasL triggers a cascade of subcellular events that results in a definable cell death process in Fas-expressing targets. Fas is a 45 kDa type I membrane protein expressed constitutively in various tissues, including spleen, lymph nodes, liver, lung, kidney and ovary. (Leithauser, F. et al. *Lab Invest* 69, 415-429 (1993); Watanabe-Fukunaga, R. et al. *J Immunol* 148, 1274-1279 (1992)). FasL is a 40 kDa type II membrane protein, and its expression is predominantly restricted to lymphoid organs and perhaps certain immune-privileged tissues. (Suda, T. et al. *Cell* 75, 1169-1178 (1993); Suda, T. et al. *J Immunol* 154, 3806-3813 (1995)). In humans, FasL can induce cytolysis of Fas-expressing cells, either as a membrane-bound form or as a 17 kDa soluble form, which is released through metalloproteinase-mediated proteolytic shedding. (Kayagaki, N. et al. *J Exp Med* 182, 1777-1783 (1995); Mariani, S. M. et al. *Eur J Immunol* 25, 2303-2307 (1995)).

The FasL/Fas system has been implicated in the control of the immune response and inflammation, the response to infection, neoplasia, and death of parenchymal cells in several organs. (Nagata et al. supra; Biancone, L. et al. *J Exp Med* 186, 147-152 (1997); Krammer, P. H. *Adv Immunol* 71, 163-210 (1999); Seino, K. et al. *J Immunol* 161, 4484-4488 (1998)). Defects of the FasL/Fas system can limit lymphocyte apoptosis and lead to lymphoproliferation and autoimmunity. A role for FasL-Fas in the pathogenesis of rheumatoid arthritis, Sjogren's syndrome, multiple sclerosis, viral hepatitis, renal injury, inflammation, aging, graft rejection, HIV infection and a host of other diseases has been proposed. (Famularo, G., et al. *Med Hypotheses* 53, 50-62 (1999)). Fas mediated apoptosis is an important component of tissue specific organ damage, such as liver injury which has been shown to be induced through the engagement of the Fas-FasL receptor system. (Kakinuma, C. et al. *Toxicol Pathol* 27, 412-420 (1999); Famularo et al. supra; Martinez, O. M. et al. *Int Rev Immunol* 18, 527-546 (1999); Kataoka, Y. et al. *Immunology* 103, 310-318 (2001); Chung, C. S. et al. *Surgery* 130, 339-345 (2001); Doughty, L. et al. *Pediatr Res* 52, 922-927 (2002)). Consequently, the FasL-Fas pathway represents an important general target for therapeutic intervention.

Monoclonal anti-FasL antibody and recombinant soluble Fas protein are well recognized potential candidate antagonists for clinical studies. (Hashimoto, H. et al. *Arthritis and Rheumatism* 41, 657-662 (1998); Kanda, Y. et al. *Bone Marrow Transplantation* 22, 751-754 (1998); Kato, K. et al. *British Journal of Haematology* 103, 1164-1166 (1998); Maggi, C. A. *Pharmacological Research* 38, 1-34 (1998)). Attempts to neutralize FasL with antibodies has been examined in a variety of animal models. (Okuda, Y. et al. *Biochem Biophys Res Commun* 275, 164-168 (2000)). While antibodies have a long half life and are highly specific they also have important limitations: (i) commercial-scale production may be either difficult or costly, (ii) conformational stability may vary with the environment of the body fluids, (iii) antibodies may be excluded from certain compartments e.g., the brain, due to failure to cross the blood/brain barrier, and (iv) they may lead to the development of neutralizing antibodies, etc. (Cho, M. J. et al. *Trends Biotechnol* 14, 153-158 (1996)).

Many disadvantages of large macromolecules can be overcome by creating small molecular inhibitors that are targeted to surface receptors or their ligands. Peptidomimetics that are constructed to resemble secondary structural features of the targeted protein represent an approach to overcome some of the limitations of macromolecules and can mimic inhibitory features of large molecules such as antibody (Park, B. W. et al. *Nat Biotechnol* 18, 194-198 (2000)) and soluble receptors. (Takasaki, W. et al. *Nat Biotechnol* 15, 1266-1270 (1997)). Recently several peptidomimetics that inhibit ligand-receptor binding and that mediate potent biological effects have been described. (Park et al. supra; Takasaki, et al. supra). These peptides represent novel small molecular tools that can act with potency comparable to or equivalent to the natural antagonist. (Takasaki et al. supra; Wrighton, N. C. et al. *Nat Biotechnol* 15, 1261-1265 (1997)).

Several studies suggest that the presence of FasL in the eye is a barrier to both inflammatory cells (Griffith, T. S., et al., *Science,* 270, 1189-92 (1995); Gao, Y., et al., *J Exp Med.,* 188, 887-96, (1998)) and development of new blood vessels (Kaplan, H. J., et al., *Nat Med.,* 5, 292-97 (1999)). The control of inflammation is known to be a component of the immune privilege of the eye (Griffith et al., 1995, supra; Griffith, T. S., et al., *Immunity,* 5, 7-16 (1996); Greil, R., A., et al., *Leukemia & Lymphoma,* 31, 477, (1998); Oconnell, J., et al., *Molecular Medicine,* 3, 294-300 (1997)). FasL expression in ocular tissue induces apoptosis in Fas+ lymphoid cells that invade the eye in response to viral infection or corneal grafting (Griffith, T. S., et al., 1995, supra; Stuart, P. M., et al., *J Clin Invest,* 99, 396-402 (1997); Chen, J. J., et al., *Science,* 282, 1714-1717 (1998); Mohan, R. R., et al., *Experimental Eye Research,* 65, 575-589 (1997)). FasL expression in the retina inhibits growth of blood vessels beneath the retina (Kaplan et al., supra), by inducing apoptosis in vascular endothelial cells that are known to express the Fas antigen. The loss of FasL expression in this region may be a predisposing factor in age related macular degeneration, allowing vessels to localize beneath the retina after penetration of Bruch's membrane. This process may lead to retinal detachment and visual loss.

FasL is also expressed in the cornea. Corneas that did not express functional FasL (gld) showed significantly greater neovascularization than normal corneas. In addition, engagement of Fas on vessels growing in vitro prevents vascular extension. These results suggest that FasL regulates neovascularization by engaging Fas on growing vessels and inducing apoptosis of the $Fas^{+}$ vascular endothelial cells. Fas/FasL interaction is also required for the antiangiogenic effects of IL-12 and IL-2 when treating murine renal carcinoma (Wigginton, J. M., et al., *J Clin Invest.,* 108, 51-62 (2001)).

Corneal neovascularization may be due to a complex interplay between several anti-angiogenic factors and Fas. This is evident from the fact that while gld and lpr mice are less prone to spontaneous neovascularization, normal development of eye is unaffected. This is similar to observations made with the immune privilege of the eye, where FasL works in concert with other inhibitory agents to control the spread of inflammation (Stuart, P. M., et al., *Invest Ophthalmol Vis Sci.,* 44, 93-98 (2003)). The role of FasL seems to be critical when the eye is challenged or stimulated with an agent that induced inflammation (Griffith et al., 1995, supra; Kaplan et al., supra) or growth factors such FGF, HGF etc. (Stuart, et. al., supra).

Recently, an inhibitor responsible for the avascularity of ocular compartments was identified in the cornea as pigment epithelium-derived factor (PEDF) (Dawson, D. W., et al., *Science,* 285, 245-48 (1999)). This protein has been shown to have neurotrophic activity (Tombran-Tink, J., et al., *J Neurosci,* 15, 4992-5003 (1995); Taniwaki, T., et al., *J Neurochem,* 68, 26-32 (1997)) but is now known as a potent anti-angiogenic molecule (Gettins, P. G., et al., *Biol Chem,* 383, 1677-82 (2002); Simonovic, M., et al., *Proc Natl Acad Sci USA,* 98, 11131-35 (2001)). It seems to be a constitutive component of ocular compartments, and neutralization of its activity permits new vessel growth into the central cornea (Dawson et al., supra). Apoptosis in endothelial cells is associated with the activity of PEDF (Stellmach, V., et al., *Proc Natl Acad Sci USA,* 98, 2593-2597 (2001); Volpert, O. V., et al., *Nat Med,* 8, 349-357 (2002)). It has been shown that PEDF inhibitory function is orchestrated via upregulation of Fas (Volpert, O. V., et al., supra) in the cornea to inhibit spontaneous neovascularization and limit induction of angiogenesis.

The pattern of Fas L expression in the eye and the results obtained when FasL expression is modified in ocular tissue suggest that Codifying Fas function might be useful for various eye related pathologies. Altering Fas function in the eye may be a useful strategy, for example, for inhibiting corneal neovascularization.

The present inventors have undertaken a structural analysis Fas-FasL interactions. The inventors have developed an interaction model of FasL and Fas created by computer assisted modeling and designed peptide mimetics based on the deduced secondary structural features of Fas. The understanding of Fas-FasL recognition features at the atomic level has allowed the inventors to design mimetics that modulate Fas signaling functions and can thus be used to treat Fas pathologies.

Accordingly, the present inventors have identified and developed peptidomimetics that alter Fas function and will therefore have therapeutic applications against disease states mediated by Fas. The mimetics were effective in inhibiting β-FGF induced corneal neovascularization in vivo, demonstrating that Fas-FasL interaction plays a significant role in regulating extension of new blood vessels into the cornea, and indicating that Fas is a therapeutic target for eye related pathologies. The in vivo biological activity of the mimetics was also validated in a murine model of Fas-dependent Con A induced hepatitis injury. Accordingly, the mimetics are therefore also useful as therapy for fulminant hepatitis.

The citation and/or discussion of a reference in this section, and throughout this specification, shall not be construed as an admission that such reference is prior art to the present invention.

SUMMARY OF THE INVENTION

In certain embodiments, the invention provides an exocyclic peptide having an amino acid sequence of a Fas surface domain that interacts with FasL.

In certain embodiments, the invention provides a Fas mimetic represented by the formula (I)

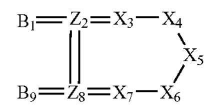

(I)

wherein:

$B_1$ and $B_9$ are independently a peptide of 1-6 amino acids, at least one of which is a hydrophobic amino acid, an aromatic moiety or a heteroaromatic moiety, $Z_2$ is a moiety that is capable of forming a covalent linkage with $B_1$, $X_3$ and $Z_8$, $Z_8$ is a moiety that is capable of forming a covalent linkage with $B_9$, $X_7$ and $Z_2$, $X_3$ is a hydrophilic amino acid or a bond, $X_4$ is an amino acid selected from aspartic acid or glutamic acid, $X_5$ is an amino acid selected from aspartic acid or glutamic acid, $X_6$ is an amino acid selected from the group consisting of histidine, lysine, arginine, asparagine or glutamine, $X_7$ is an aromatic moiety or a heteroaromatic moiety, "—" is a covalent linkage comprising an amide, substituted amide or an isostere of amide thereof, and "═" is a covalent linkage, or a pharmaceutically acceptable salt, metabolite or prodrug thereof.

Preferably, the mimetic of formula (I) is a peptide comprising an amino sequence selected from the group consisting of YCDEGHLCY (SEQ ID NO: 1), YCDEGLCY (SEQ ID NO: 2), YCDEGYFCY (SEQ ID NO: 3), YCDEGEYCY (SEQ ID NO: 4), YCDEHFCY (SEQ ID NO:5), YCDEHGLCY (SEQ ID NO: 6), YCDEHGQCY (SEQ ID NO: 7), YCDEKFCY (SEQ ID NO: 8), and YCDEQFCY (SEQ ID NO: 9), wherein the cysteine residues of said peptide are preferably joined by a covalent bond to form a cyclic peptide. More preferably, the mimetic of formula (I) is a peptide comprising an amino sequence selected from the group consisting of YCDEHFCY (SEQ ID NO: 5), YCDEKFCY (SEQ ID NO: 8) and YCDEQFCY (SEQ ID NO: 9) wherein the cysteine residues of said peptide are preferably joined by a covalent bond to form a cyclic peptide.

In other embodiments, the invention provides mimetics comprising an amino acid sequence selected from the group consisting of YCNSTVCY (SEQ ID NO: 10), YCDKAEHFCY (SEQ ID NO: 11), YCNTRTQNTCY (SEQ ID NO: 12), YCQEKEYCY (SEQ ID NO: 13), and YCQERKEYCY (SEQ ID NO: 14).

In other embodiments, the invention is directed to a method of preventing or treating a FAS-related pathology comprising administering to a mammal (e.g., a human) suffering from said FAS-related pathology a therapeutically effective amount of the foregoing mimetics.

The invention also provides pharmaceutical compositions comprising the aforementioned mimetics.

In other embodiments, the invention is directed to a method of inhibiting Fas receptor-Fas ligand interaction comprising exposing Fas or FasL to an effective amount of the aforementioned mimetics to inhibit said interaction.

BRIEF DESCRIPTION OF THE DRAWINGS

FIG. 1A-B depicts the three dimensional structure of the binding site in FasL/Fas complex. (A) Interaction between a FasL dimer and Fas peptide mimetics Kp1, Kp2, Kp3, Kp4 and Kp7. (B) Putative solution structure of peptide mimetic Kp7-6.

DETAILED DESCRIPTION

Figure 2A:
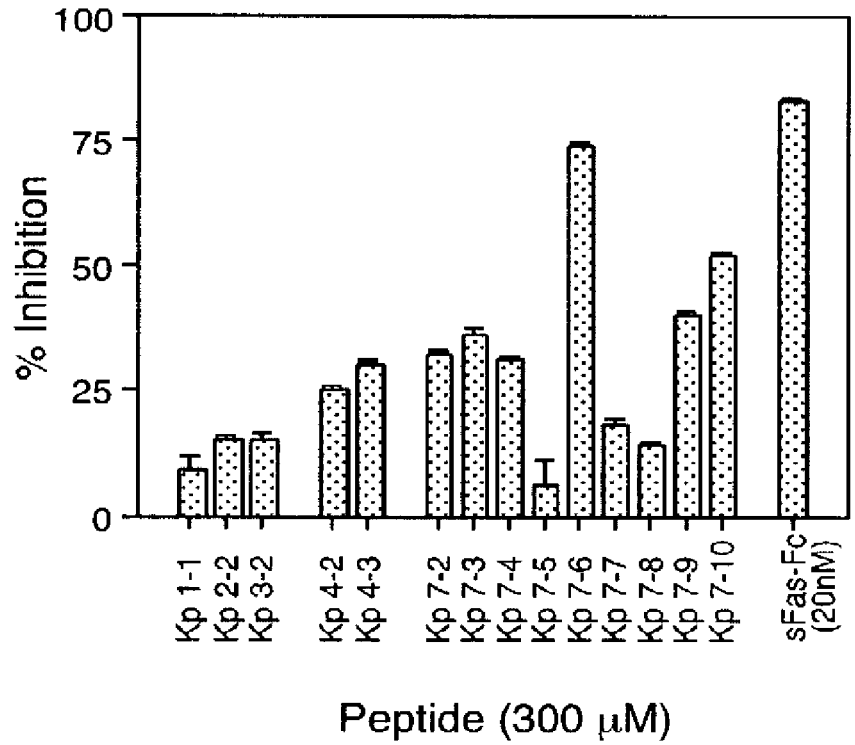
FIG. 2A-B illustrates inhibition of FasL binding to Fas-receptor by exocyclic mimetics in a binding assay.
Figure 2B:
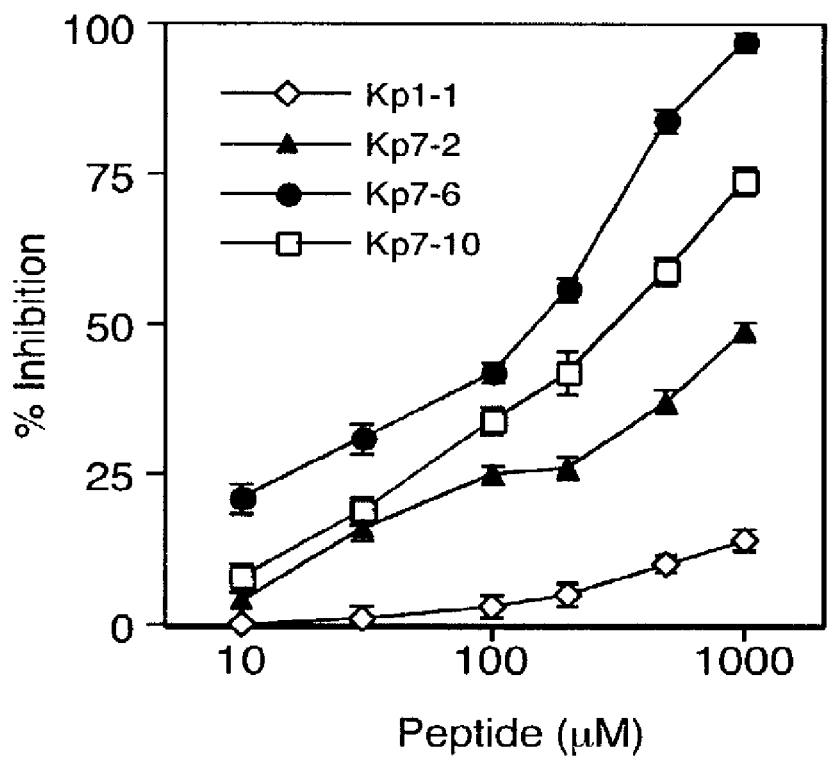
Figure 3A:
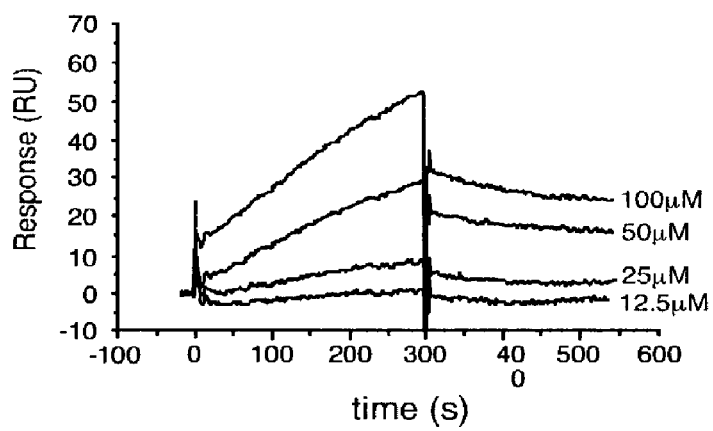
FIG. 3A-B depicts a surface plasmon resonance (biosensor) analysis of mimetic binding to immobilized FasL.
Figure 3B:
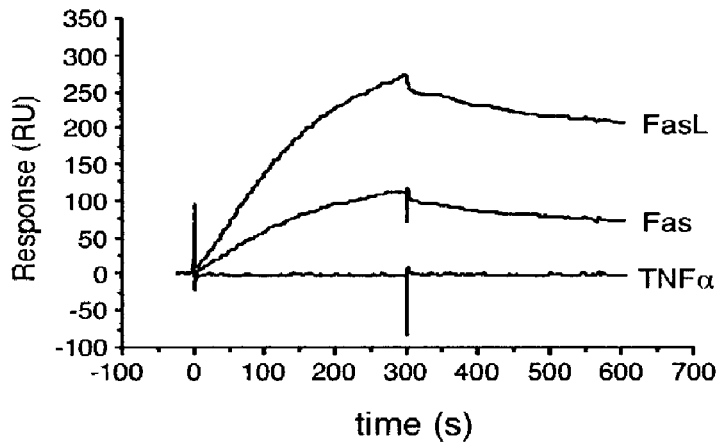
Figure 4:
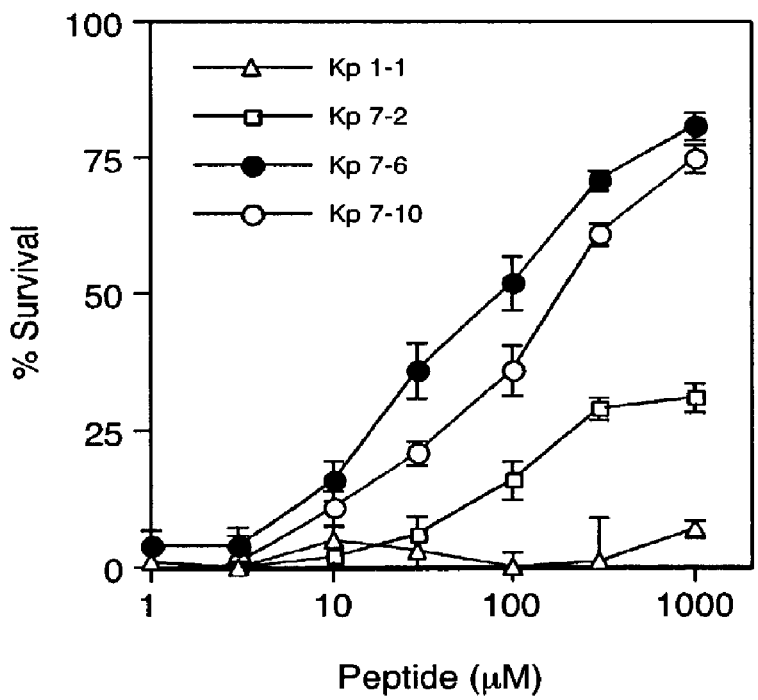
FIG. 4 depicts inhibition of FasL-induced cytolysis in Jurkat cells by the antagonistic peptides.

The present invention is concerned with mimetics that are antagonists of the Fas receptor (Fas)-Fas ligand (FasL) signaling system and methods of using such mimetics. The invention is based in part on the findings that sites on Fas that function in the binding of FasL can be identified by comparison to the TNF receptor and that peptide mimetics of the sites identified on Fas act to inhibit binding of FasL to Fas and inhibit Fas function, i.e., the mimetics are antagonists of FasL binding and of Fas signaling and function. The mimetics are therefore useful in the treatment of Fas-related pathologies.

Hence, the invention provides exocyclic peptide mimetics comprising an amino acid sequence of a Fas surface domain that interacts with FasL or derived from an amino acid sequence of a Fas surface domain that interacts with FasL.

The invention provides Fas mimetics represented by formula (I)

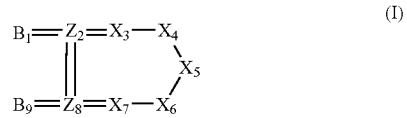
(I)

wherein:
B$_1$ and B$_9$ are independently a peptide of 1-6 amino acids, at least one of which is a hydrophobic amino acid, an aromatic moiety or a heteroaromatic moiety,
Z$_2$ is a moiety that is capable of forming a covalent linkage with B$_1$, X$_3$ and Z$_8$,
Z$_8$ is a moiety that is capable of forming a covalent linkage with B$_9$, X$_7$ and Z$_2$,
X$_3$ is a hydrophilic amino acid or a bond,
X$_4$ is an amino acid selected from aspartic acid or glutamic acid,
X$_5$ is an amino acid selected from aspartic acid or glutamic acid,
X$_6$ is an amino acid selected from the group consisting of histidine, lysine, arginine, asparagine or glutamine,
X$_7$ is an aromatic moiety or a heteroaromatic moiety,
"—" is a linkage comprising an amide, substituted amide or an isostere of amide thereof, and
"=" is a covalent linkage,
or a pharmaceutically acceptable salt, metabolite or prodrug thereof.

B$_1$ and B$_9$ independently are exocyclic portions of mimetics of formula (I) that are comprised of, e.g., exocyclic amino acid residues. Z$_2$, X$_3$, X$_4$, X$_5$, X$_6$, X$_7$ and Z$_8$ comprise the cyclicized portion of mimetics of formula (I). Z$_2$ and Z$_8$ are further linking moieties, preferably linking amino acids.

Preferably, Fas mimetics of the invention are conformationally restrained peptides. Most preferably, such conformationally restrained peptides are cyclicized peptides comprising a cyclicized portion, one or more exocyclic region, one or more linking moiety and an active region.

Independent preferred moieties for the formula I are as follows: Z$_2$ is cysteine; Z$_8$ is cysteine; X$_3$ is a bond; X$_4$ is aspartic acid; X$_5$ is glutamic acid; X$_7$ is phenylalanine; and X$_7$ is an aromatic amino acid.

The following are also independent preferences: B$_1$ is tyrosine; B$_9$ is tyrosine; both B$_1$ and B$_9$ are tyrosine; B$_1$ is —R$_1$-R$_2$, where R$_1$ is an aromatic amino acid linked to Z$_2$ and R$_2$ is a peptide of 1-5 amino acids; B$_9$ is —R$_3$—, where R$_3$ is an aromatic acid linked to Z$_8$ and R$_4$ is a peptide of 1-5 amino acids.

Also preferred is a mimetic of formula (I) comprising an amino sequence selected from the group consisting of YCDEGHLCY (SEQ ID NO: 1), YCDEGLCY (SEQ ID NO: 2), YCDEGYFCY (SEQ ID NO: 3), YCDEGEYCY (SEQ ID NO: 4), YCDEHFCY (SEQ ID NO: 5), YCDEHGLCY (SEQ ID NO: 6), YCDEHGQCY (SEQ ID NO: 7), YCDEKFCY (SEQ ID NO: 8) and YCDEQFCY (SEQ ID NO: 9), wherein the cysteine residues of said amino acid sequence are joined by a covalent bond, to form a cyclic peptide. More preferably, a mimetic of formula (I) comprises an amino sequence selected from the group consisting of YCDEHFCY (SEQ ID NO: 5), YCDEKFCY (SEQ ID NO: 8) and YCDEQFCY (SEQ ID NO: 9), wherein the cysteine residues of said amino acid sequence are joined by a covalent bond, to form a cyclic peptide.

Also provided for use in the invention is a mimetic comprising an amino acid sequence selected from the group consisting of YCNSTVCY (SEQ ID NO: 10), YCDKAEHFCY (SEQ ID NO: 11), YCNTRTQNTCY (SEQ ID NO: 12), YCQEKEYCY (SEQ ID NO: 13), and YCQERKEYCY (SEQ ID NO: 14).

Preferred mimetics provided in the invention are in the range of about 5 to about 100 amino acids in length. Further preferred mimetics provided in the invention are in the range of about 5 to about 50 amino acids in length, or in the range of about 10 to about 50 amino acids in length. Still further preferred mimetics provided in the invention are in the range of about 5 to about 40 amino acids in length, or in the range of about 10 to about 40 amino acids in length. Still further preferred mimetics provided in the invention are in the range of about 5 to about 30 amino acids in length, or in the range of about 10 to about 30 amino acids in length. Still further preferred mimetics provided in the invention are in the range of about 5 to about 20 amino acids in length, or in the range of about 10 to about 20 amino acids in length. Most preferred mimetics provided in the invention are in the range of about 5 to about 10 amino acids in length.

DEFINITIONS

Amino acid residues used in the present invention may be recited by their full name or by reference to either the three letter or single letter amino acid code (see, e.g., Table 5.1 of Mathews & van Holde, *Biochemistry*, Second Edition (Benjamin/Cumings Publishing Company, Inc., New York) at page 131). The mimetics that are encompassed within the scope of the invention are partially defined in terms of amino acid residues of designated classes. The amino acids may be generally categorized into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains. Hydrophobic amino acids include amino acids having aromatic or apolar side chains. Apolar amino acids may be further subdivided to include, among others, aliphatic amino acids. The definitions of the classes of amino acids as used herein are as follows:

The term "hydrophobic amino acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

The term "aromatic amino acid" refers to a hydrophobic amino acid having a side chain containing at least one ring having a conjugated pi-electron system (aromatic group). The aromatic group may be further substituted with substituent groups such as alkyl, alkenyl, alkynyl, hydroxyl, sulfanyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

The term "hydrophilic amino acid" refers to an amino acid having a side chain that is capable of bonding to solvent molecules in an aqueous solution. Examples of genetically encoded hydrophilic amino acids include Ser and Lys. Examples of non-encoded hydrophilic amino acids include Cit and hCys.

The term "heteroaromatic moiety" refers to an aromatic moiety wherein one or more of the ring carbon atoms is replaced with another atom such as, for example, nitrogen, oxygen or sulfur. Typical heteroaromatic moieties include, but are not limited to, pyran, pyrazole, pyridine, pyrrole, pyrazine, pyridazine, pyrimidine, pyrrolizine, quinazoline, quinoline, quinolizine, quinoxaline, selenophene, thiophere, tellurophene, xanthene, and the like.

Additional examples of amino acids and related compounds are found in U.S. Pat. No. 6,265,535.

As used herein, the term "mimetic" refers to compounds which mimic the activity of a peptide. Mimetics may themselves be peptides. Mimetics may also be non-peptides and/or may comprise amino acids linked by non-peptide bonds, e.g., without limitation, psi bonds (see, e.g., Benkirane, N., et al. *J. Biol. Chem.*, 271:33218-33224 (1996)). U.S. Pat. No. 5,637, 677 and its parent applications contain detailed guidance on the production of mimetics. Preferred mimetics are "conformationally constrained" peptides. Also preferred are cyclic mimetics. Further preferred are cyclic mimetics comprising at least one exocyclic domain, a linking moiety (e.g., a linking amino acid) and an active region.

As used herein, the terms "constrained peptides" and "conformationally constrained peptides" are used interchangeably and are meant to refer to peptides which, e.g., through intramolecular bonds, are conformationally stable and remain in a restricted conformation.

As used herein, the term "exocyclic amino acid residue" is meant to refer to an amino acid residue that is linked directly or indirectly to a cyclicized peptide but which is not within the portion of the peptide that makes up the circularized structure.

As used herein, the term "exocyclic portion" is meant to refer to an amino acid sequence having one or more amino acid residues which are linked to cyclicized peptide but which are not within the portion of the peptide that makes up the circularized structure.

As used herein, the term "linking moiety" is meant to refer to a molecular component or functional group which is capable of forming bonds with three amino acids.

As used herein, the term "linking amino acid residue" is meant to refer to an amino acid residue that is a linking moiety.

As used herein, the term "active region" is meant to refer to the amino acid sequence of the portion of a mimetic that directly interacts with a receptor or receptor ligand, wherein the interaction is characterized by an affinity between the active region of the mimetic and the receptor or receptor ligand.

The term "Fas mimetic" refers to a peptide mimetic that is derived from a Fas peptide; i.e., a Fas mimetic of the invention is a compound that mimics a Fas peptide (a peptide derived from Fas). Preferred Fas mimetics are mimetics of a peptide derived from and/or corresponding to a Fas surface domain. Further preferred are Fas mimetics that are mimetics of a peptide derived from and/or corresponding to a Fas surface loop domain. Exemplary Fas peptides are provided, infra, in Table 1. Particularly preferred Fas mimetics of the invention are mimetics of Fas Kp7 surface domain peptides.

Fas mimetics are preferably derived from human or mouse Fas. More preferably, Fas mimetics are derived from human Fas, e.g., without limitation, human Fas. Most preferably, mimetics are derived from human Fas with the mature amino acid sequence:

```
                                            (SEQ ID NO: 15)
RLSSKSVNAQVTDINSKGLELRKTVTTVETQNLEGLHHDGQFCHKPCPPG

ERKARDCTVNGDEPDCVPCQEGKEYTDKAHFSSKCRRCRLCDEGHGLEVE

INCTRTQNTKCRCKPNFFCNSTVCEHCDPCTKCEHGIIKECTLTSNTKCK

EEGSRSNLGWLCLLLLPIPLIVWVKRKEVQKTCRKHRKENQGSHESPTLN

PETVAINLSDVDLSKYITTIAGVMTLSQVKGFVRKNGVNEAKIDEIKNDN

VQDTAEQKVQLLRNWHQLHGKKEAYDTLIKDLKKANLCTLAEKIQTIILK

DITSDSENSNFRNEIQSLV
```

Preferred Fas mimetics of the invention are capable of interacting with (e.g., binding to) either Fas, FasL or both Fas and FasL. Fas mimetics may therefore modulate Fas activity (in particular, Fas mediated signaling), for example as antagonists, agonists, or inverse agonists. For example, in certain embodiments a Fas mimetic of the invention may inhibit binding of FasL to Fas, and may thereby inhibit Fas activity. In other embodiments (that are preferably practiced either in the absence of or at very low concentrations of FasL) a Fas mimetic of the invention may bind to and activate Fas.

As used herein, the term "surface domain" refers to a domain of a protein comprising one or more solvent accessible amino acid. A surface domain make include, e.g., 1, 2, 3, 4, 5, 6, 7, 8, 9, 10, 11, 12, 13, 14, 15, 16, 17, 18, 19, or 20 solvent accessible amino acids. A surface domain may also include greater than 20 solvent accessible amino acids. Preferably, each amino acid in a surface domain is a solvent accessible amino acid. Solvent accessible amino acids and hence surface domains may be identified using methods well known in the art (see, e.g., Jones et al., *J. Mol. Biol.*, 272:121-132 (1997) and Samanta, U. et al., *Prot. Eng.*, 15:659-667 (2002)).

Solvent accessibility of an amino acid is expressed as a value from 0.0 (buried) to 1.0 completely accessible. Preferably, a surface domain comprises at least one amino acid with a solvent accessibility of at least about 0.3. More preferably, a surface domain comprises at least one amino acid with a solvent accessibility of at least about 0.4, 0.5, 0.6 or 0.7. More preferably, a surface domain comprises at least one amino acid with a solvent accessibility of at least about 0.8, 0.9 or 0.95. Further preferred is where a surface domain comprises about 2, 3, 4, 5, 6, 7, 8, 9, or 10 amino acids with a solvent accessibility of at least 0.3, or comprises at least about 2, 3, 4, 5, 6, 7, 8, 9, or 10 amino acids with a solvent accessibility of at least about 0.3. Further preferred is where a surface domain comprises about 2, 3, 4, 5, 6, 7, 8, 9, or 10 amino acids with a solvent accessibility of at least about 0.4, 0.5, 0.6, or 0.7, or comprises at least about 2, 3, 4, 5, 6, 7, 8, 9, or 10 amino acids with a solvent accessibility of at least about 0.4, 0.5, 0.6, or 0.7. Further preferred is where a surface domain comprises about 2, 3, 4, 5, 6, 7, 8, 9, or 10 amino acids with a solvent accessibility of at least about 0.8, 0.9, or 0.95, or comprises at least about 2, 3, 4, 5, 6, 7, 8, 9, or 10 amino acids with a solvent accessibility of at least about 0.8, 0.9, or 0.95.

Also preferred is where a surface domain consists of about 2, 3, 4, 5, 6, 7, 8, 9, or 10 amino acids with a solvent accessibility of at least about 0.3, or consists of at least about 2, 3, 4, 5, 6, 7, 8, 9, or 10 amino acids with a solvent accessibility of at least about 0.3. Further preferred is where a surface domain consists of about 2, 3, 4, 5, 6, 7, 8, 9, or 10 amino acids with a solvent accessibility of at least about 0.4, 0.5, 0.6, or 0.7, or consists of at least about 2, 3, 4, 5, 6, 7, 8, 9, or 10 amino acids with a solvent accessibility of at least about 0.4, 0.5, 0.6, or 0.7. Further preferred is where a surface domain consists of about 2, 3, 4, 5, 6, 7, 8, 9, or 10 amino acids with a solvent accessibility of at least about 0.8, 0.9, or 0.95, or consists of at least about 2, 3, 4, 5, 6, 7, 8, 9, or 10 amino acids with a solvent accessibility of at least about 0.8, 0.9, or 0.95.

As used herein, the term "treatment" refers to administering an active agent to lessen the severity or the likelihood of the re-occurrence of a pre-existing condition. Hence, "treatment" encompasses, for example and without limitation, ameliorating at least one symptom associated with a condition or reducing the rate of occurrence or re-occurrence of a condition.

As used herein, the term "preventing" refers to the lessening of the likelihood of the occurrence of a condition.

As used herein, a "subject in need of treatment of" or a "subject suffering from" a condition is a mammal (e.g., human) that manifests at least one symptom of a condition or that is at risk of developing or re-developing the particular condition to be treated.

As used herein, a "therapeutically effective amount" of an agent is an amount sufficient to ameliorate at least one symptom associated with a pathological, abnormal or otherwise undesirable condition, an amount sufficient to prevent or lessen the probability that such a condition will occur or re-occur, or an amount sufficient to delay worsening of such a condition.

As used herein, a "Fas-related pathology" is a pathological condition that can be treated by increasing or decreasing activity (i.e., signaling) of Fas. A "Fas-related pathology" is preferably treated with an antagonist of Fas activity. More preferably, said antagonist binds to one or both of Fas or FasL to lower Fas activity. Alternatively, in certain embodiments, a "Fas-related pathology" may be treated with an agonist of Fas activity. Examples of "Fas-related pathologies" include, without limitation, pathologies related to lymphocyte apoptosis leading to abnormal lymphoproliferation and autoimmunity. Additional examples include, without limitation, aging and cell death (e.g., in the skin and other organs), visual loss, rheumatoid arthritis, Sjogren's syndrome, multiple, viral hepatitis, renal injury, HIV infection, and angiogenesis. See also Famularo et al. supra. The inhibition of FasL and Fas antigen interactions has also been used to prevent transplantation rejections. Mimetics of the invention which inhibit the binding of Fas with FasL may be used to augment immune responses in certain settings.

In a preferred embodiment, mimetics of the invention are used to treat visual loss or other ocular disorder either with or without coincident neovascularization. In a preferred embodiments, the mimetics of the invention are used to treat visual loss or other ocular disorder with coincident neovascularization. Examples of ocular disorder include, without limitation, macular degeneration, e.g, age-related macular degeneration.

A "metabolite" of a compound disclosed herein is a derivative of a compound which is formed when the compound is metabolized. The term "active metabolite" refers to a biologically active derivative of a compound which is formed when the compound is metabolized. The term "metabolized" refers to the sum of the processes by which a particular substance is changed in the living body. In brief, all compounds present in the body are manipulated by enzymes within the body in order to derive energy and/or to remove them from the body. Specific enzymes produce specific structural alterations to the compound. For example, cytochrome P450 catalyses a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Further information on metabolism may be obtained from *The Pharmacological Basis of Therapeutics*, 9th Edition, McGraw-Hill (1996), pages 11-17.

Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

A "prodrug" of a compound disclosed herein is an inactive substance that converts into an active form of the disclosed compounds in vivo when administered to a mammal.

The compounds of the present invention are related to mimetics of Fas as disclosed above, including all enantiomers, diastereomers, crystalline forms, hydrates, solvates or pharmaceutically acceptable salts thereof, as well as active metabolites of these mimetics having the same type of activity.

An antagonist of Fas is a substance which diminishes or abolishes the effect of a ligand (agonist) which typically activates Fas receptor, e.g., FasL. The antagonist may be, for example, a chemical antagonist, a pharmacokinetic antagonist, an antagonist by receptor block, a non-competitive antagonist or a physiological antagonist. In a preferred embodiment, the antagonist is a chemical antagonist or an antagonist by receptor block. The antagonist is preferably a Fas mimetic. Further preferred, the antagonist is a mimetic of Fas peptide Kp1, Kp2, Kp3, Kp4, or Kp7.

A chemical antagonist is a substance wherein the antagonist binds the ligand in solution so the effect of the ligand is lost. A pharmacokinetic antagonist is one which effectively reduces the concentration of the ligand at its site of action, for example, by increasing the rate of metabolic degradation of the active ligand. Antagonism by receptor-block involves two important mechanisms: reversible competitive antagonism and irreversible, or non-equilibrium competitive antagonism. Reversible competitive antagonism occurs when the rate of dissociation of the antagonist molecules is sufficiently high such that, on addition of the ligand, displacement of chemical antagonist molecules from the receptors effectively occurs. Of course the ligand cannot evict a bound antagonist molecule, or vice versa. Irreversible or non-equilibrium competitive antagonism occurs when the antagonist dissociates very slowly, or not at all, from the receptor with the result that no change in the antagonist occupancy takes place when the ligand is applied. Thus, the antagonism is insurmountable. Non-competitive antagonism describes the situation where the antagonist exerts its blocking action at some point in the signal transduction pathway leading to the production of a response by the ligand.

Mimetics of the invention are preferably antagonists of Fas. More preferably, mimetics used in the invention are selective antagonists of Fas. A selective antagonist of Fas is one which antagonizes Fas, but antagonizes other receptors of the TNF family of receptors only weakly or substantially not at all. Most preferred mimetic antagonists are those which selectively antagonize Fas receptor at low concentration, for example, those that cause a level of antagonism of 50% or greater at a concentration of 1000 mM or less. Selective Fas mimetic antagonists can thus typically exhibit at least a 10-fold, preferably a 100-fold and most preferably a 1000-fold greater activity for Fas than at other TNF receptors.

Preferred Embodiments

Fas mimetics of the invention preferably have one or more of the following properties:

(1) Significant Inhibition of FasL Binding to Fas:

Mimetics preferably exhibit antagonist potency (measured as $IC_{50}$) between 1 nM and 500 mM. Without limiting the present disclosure, as described in more detail below, potency may be measured by determining the antagonist activity of mimetics in vivo or in vitro, including cell extracts or fractions of extracts. Inhibitory potency may also be determined using, as non-limiting examples, native or recombinant Fas, and/or soluble Fas. Fas binding may be determined using methods that are well known to those skilled in the art, such as ELISA and proliferation by MTT (Hansen et al., *J. Immunol. Methods* 199, 203-210 (1989))

(2) Selectivity:

Preferred mimetics exhibit at least about 10-fold greater antagonist potency for Fas, compared to other TNF receptors. More preferred are compounds that exhibit about 100-fold greater antagonist for Fas, compared to other TNF receptors. Most preferred are compounds that exhibit about 1000-fold greater antagonist for Fas, compared to other TNF receptors.

(3) Binding to FasL:

Mimetics preferably bind to FasL and inhibit the interaction of FasL and Fas. The binding affinity of mimetics to FasL can be described by different parameters, e.g., $k_{on}$, $k_{off}$ and $K_D$. In preferred embodiments, the mimetics have affinities for FasL represented by values of $k_{on}$ greater than $10\ M^{-1}s^{-1}$, $k_{off}$ of less than $10^{-3}s^{1}$ or $K_D$ of less than $10^{-4}$ M. More preferably, mimetics have affinities for FasL represented by values of $k_{on}$ greater than $10^2\ M^{-1}s^{-1}$, $k_{off}$ of less than $10^{-4}s^{-1}$ or $K_D$ of less than $10^{-5}$ M. Most preferably, mimetics have affinities for FasL represented by values of $k_{on}$ greater than $10^3 M^{-1}s^{-1}$, $k_{off}$ of less than $10^{-5}\ s^{-1}$ or $K_D$ of less than $10^{-6}$ M.

Accordingly, mimetics having one or more of these properties are candidates for use in treatment of Fas-related pathologies in mammals and especially in humans.

Mimetics with one or more of the above properties can further be tested for biological activity using assays that measure Fas function in vitro or in vivo.

Measurement of mimetic biological activity can be determined in vitro, e.g., by measuring inhibition of Fas-L induced cytotoxicity or by inhibition of Fas-L induced apoptosis in cell culture, as described below in Examples 4 and 5, respectively. Alternatively, mimetic biological activity may also be measured by directly or indirectly measuring signaling aspects of Fas activity, such as caspase activity, NF-κB activation, and/or other downstream mediators of Fas signaling.

A useful animal model for measurement of Fas activity in vivo is the Con A-induced hepatitis model described in Example 6. This assay is a murine model of human autoimmune hepatitis. (Tiegs, G. et al. *J Clin Invest* 90, 196-203 (1992)). T cell activation plays a crucial role in the process of Con A-induced hepatitis, because severe combined immunodeficiency disorder (SCID) mice and athymic nude mice, which lack mature T cells, are resistant to the damage induced by Con A. (Tiegs et al. supra; Mizuhara, H. et al. *J Exp Med* 179, 1529-1537 (1994). The hepatic injury seems to be induced by several different mechanisms, such as those involving Fas-FasL (Seino, K. et al. *Gastroenterology* 113, 1315-1322 (1997); Tagawa, Y. et al. *Eur J Immunol* 28, 4105-4113 (1998); Tagawa, Y. et al. *J Immunol* 159, 1418-1428 (1997)), the perforin-granzyme system (Watanabe, Y. et al. *Hepatology* 24, 702-710 (1996)), IFN-γ (Tagawa et al. supra; Kusters, S. et al. *Gastroenterology* 111, 462-471 (1996)) and TNF-α-mediated cytotoxicity (Mizuhara et al. supra; Toyabe, S. et al. *J Immunol* 159, 1537-1542 (1997); Gantner, F. et al. *Exp Cell Res* 229, 137-146 (1996); Gantner, F. et al. *Hepatology* 21, 190-198 (1995); Kusters, S. et al. *Eur J Immunol* 27, 2870-2905 (1997); Ksontini, R. et al. *J Immunol* 160, 4082-4089 (1998)). (Mizuhara, H. et al. *J Exp Med* 179, 1529-1537 (1994). Hepatic damage is primarily dependent upon the Fas-FasL system, because FasL defective gld/gld mice or Fas defective lpr/lpr mice are resistant to liver injury induced by Con A treatment. (Tagawa et al. supra; Tagawa et al. supra).

Design of Mimetics:

According to preferred embodiments a mimetic is designed based on a known region of FAS. In preferred embodiments, the mimetic mimics an extracellular domain of an Fas, more preferably a cystine knot region of Fas. Most preferably, the mimetic is based on the Fas Kp7 domain.

Identification of Fas peptides on which to base mimetics can be performed using computer modeling and structural analysis. For instance, Example 1, infra, describes one embodiment in which an interaction model of FasL and Fas was created by computer assisted modeling, and used to design peptide mimetics based on deduced secondary structural features of Fas. In such an embodiment, a skilled user may define optimal interactions of Fas surfaces that are consistent with either available biological data or structural surface complementarity. Peptide mimetics can then be designed and synthesized for all secondary structures involved in such interactions, typically corresponding to about five mimetic compounds. Each compound may be modified as described, e.g., in U.S. Pat. Nos. 6,100,377 and 6,265,535. The mimetic compounds thus obtained can then be tested, e.g., using methods described in this application, for their activity as Fas agonists or antagonists.

Reducing a macromolecule to a small molecule with similar function is a general chemical problem. There have been some attempts to design mini-proteins by transplanting functional units onto suitable scaffolds (Vita et al, *Biopolymers* 47, 93-100 (1998)) and minimizing antibodies to single chain antibodies (Magliani et al., *Nature Biotechnol.* 15, 155-158 (1997)).

It is now established that conformation constrained peptides are more bioactive than unconstrained ones. In recent years, the chemistry of peptide cyclization by solid phase synthesis and other methods has improved dramatically (Burgess et al (1996) in *Solid phase syntheses of peptidomimetics* (American Chemical Society, Washington D.C.) pp. ORGN-157; Goodman & Shao, *Pure Appl. Chem.* 68, 1303-1308 (1996); Hanessian et al, *Tetrahedron* 53, 12789-12854 (1997); Koskinen & Hassila, *Acta Chem. Scand.* 50, 323-327 (1996); Kuhn et al, *Tetrahedron* 53, 12497-12504 (1997); Waid et al, *Tetrahedron Lett.* 37, 4091-4094 (1996); Zuckermann, *Curr. Opin. Struct. Biol.* 3, 580-584 (1993)) providing more opportunity to develop peptides into peptidomimetics.

General principles to create cyclic peptide mimetics that have been adopted and in some cases (such as eptifitimide (Integrilin) a glycoprotein llb llla inhibitor (COR Therapeutics)) have become clinically available. Aromatic residues placed at the termini of cyclically constrained small peptides increase the activity of mimetics (Takasaki et al., *Nat. Biotechnol.* 15, 1266-1270 (1997); Zhang et al., *Nature Biotechnol.* 14, 472-475 (1996)). Employing such modifications has allowed creation of high affinity mimetics of antibody mimics based on CDRs (Park et al., *Nature Biotechnol.* 18, 194-198 (2000)), CD4 (Zhang et al., *Nature Biotechnol.* 15, 150-154 (1997)), IL4 receptor loop mimetics, anti-CD3 antibody mimics, and TNF cystine knot mimetic that affect TNFα binding to its receptor (Takasaki et al., *Nature Biotechnol.* 15, 1266-1270 (1997)).

Chemical Synthesis:

The mimetics of the invention may be prepared using virtually any art-known technique for the preparation of peptides and peptide analogues. For example, the peptides may be prepared in linear or non-cyclized form using conventional solution or solid phase peptide syntheses and cyclized using standard chemistries. Preferably, the chemistry used to cyclize the peptide will be sufficiently mild so as to avoid substantially degrading the peptide. Suitable procedures for synthesizing the peptides described herein as well as suitable chemistries for cyclizing the peptides are well known in the art.

Formation of disulfide linkages, if desired, is generally conducted in the presence of mild oxidizing agents. Chemical, enzymatic or photolytic oxidation agents may be used. Various methods are known in the art, including those described, for example, by Tam, J. P. et al., 1979, *Synthesis* 955-957; Stewart et al., 1984, *Solid Phase Peptide Synthesis*, 2d Ed., Pierce Chemical Company Rockford, Ill.; Ahmed et al., 1975, *J. Biol. Chem.* 250:8477-8482; and Pennington et al., 1991 *Peptides* 1990 164-166, Giralt and Andreu, Eds., ESCOM Leiden, The Netherlands. An additional alternative is described by Kamber et al., 1980, *Helv Chim Acta* 63:899-915. A method conducted on solid supports is described by Albericio, 1985, *Int. J. Peptide Protein Res.* 26:92-97. Any of these methods may be used to form disulfide linkages in the peptides of the invention.

Recombinant Synthesis:

If the peptide is composed entirely of gene-encoded amino acids, or a portion of it is so composed, the peptide or the relevant portion may also be synthesized using conventional recombinant genetic engineering techniques. The isolated peptides, or segments thereof, are then condensed, and oxidized, as previously described, to yield a cyclic peptide.

For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the linear form of the cyclic peptide. Depending on the expression system used, the expressed peptide is then isolated by procedures well-established in the art. Methods for recombinant protein and peptide production are well known in the art (see, e.g., Maniatis et al., 1989, *Molecular Cloning A Laboratory Manual*, Cold Spring Harbor Laboratory, N.Y.; and Ausubel et al., 1989, *Current Protocols in Molecular Biology*, Greene Publishing Associates and Wiley Interscience, N.Y.).

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, *Nature* 310:511-514), or the coat protein promoter of TMV (Takamatsu et al., 1987, *EMBO J.* 6:307-311) may be used; alternatively, plant promoters such as the small subunit of RUBISCO (Coruzzi et al., 1984, *EMBO J.* 3:1671-1680; Broglie et al., 1984, *Science* 224:838-843) or heat shock promoters, e.g., soybean hsp17.5-E or hsp17.3-B (Gurley et al., 1986, *Mol. Cell. Biol.* 6:559-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, *Methods for Plant Molecular Biology*, Academic Press, NY, Section VIII, pp. 421-463; and Grierson & Corey, 1988, *Plant Molecular Biology*, 2d Ed., Blackie, London, Ch. 7-9.

In one insect expression system that may be used to produce the peptides of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, *J. Virol.* 46:584; Smith, U.S. Pat. No. 4,215,051). Further examples of this expression system may be found in Current *Protocols in Molecular Biology*, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan et al., 1984, *Proc. Natl. Acad. Sci. USA* 81:3655-3659). Alternatively, the vaccinia 7.5 K promoter may be used, (see, e.g., Mackett et al., 1982, *Proc. Natl. Acad. Sci. USA* 79:7415-7419; Mackett et al., 1984, *J. Virol.* 49:857-864; Panicali et al., 1982, *Proc. Natl. Acad. Sci. USA* 79:4927-4931).

Other expression systems for producing linear or non-cyclized forms of the cyclic peptides of the invention will be apparent to those having skill in the art.

Purification of the Peptides and Peptide Analogues:

The peptides and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art.

For affinity chromatography purification, any antibody which specifically binds the peptides or peptide analogues may be used. For the production of antibodies, various host animals, including but not limited to rabbits, mice, rats, etc., may be immunized by injection with a linear or cyclic peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Koehler and Milstein, 1975, *Nature* 256:495-497, the human B-cell hybridoma technique, Kosbor et al., 1983, *Immunology Today* 4:72; Cote et al., 1983, *Proc. Natl. Acad. Sci. USA* 80:2026-2030 and the EBV-hybridoma technique (Cole et al., 1985, *Monoclonal Antibodies and Cancer Therapy*, Alan R. Liss, Inc., pp. 77-96 (1985)). In addition, techniques developed for the production of "chimeric antibodies" (Morrison et al., 1984, *Proc. Natl. Acad. Sci. USA* 81:6851-6855; Neuberger et al., 1984, *Nature* 312:604-608; Takeda et al., 1985, *Nature* 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce cyclic peptide-specific single chain antibodies.

Antibody fragments which contain deletions of specific binding sites may be generated by known techniques. For example, such fragments include but are not limited to F(ab').sub.2 fragments, which can be produced by pepsin digestion of the antibody molecule and Fab fragments, which can be generated by reducing the disulfide bridges of the F(ab').sub.2 fragments. Alternatively, Fab expression libraries may be constructed (Huse et al., 1989, *Science* 246:1275-1281) to allow rapid and easy identification of monoclonal Fab fragments with the desired specificity for the cyclic peptide of interest.

The antibody or antibody fragment specific for the desired cyclic peptide can be attached, for example, to agarose, and the antibody-agarose complex is used in immunochromatography to purify cyclic peptides of the invention. See, Scopes, 1984, *Protein Purification Principles and Practice*, Springer-Verlag New York, Inc., NY, Livingstone, 1974, Methods Enzymology: Immunoaffinity Chromatography of Proteins 34:723-731.

Formulation and Routes of Administration:

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc., as are well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc., formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the mimetics of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

Effective Dosage:

The compounds of the invention will generally be used in an amount effective to achieve the intended purpose. For use to treat or prevent FAS-related pathologies, the compounds of the invention, or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that inhibits 50% of Fas:Fas-L binding interactions). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.01 to about 25 mg/kg/day, preferably from about 0.1 to about 10 mg/kg/day and more preferably from about 0.5 to about 5 mg/kg/day. Also preferred are total daily dosages from about 25 to about 1000 mg per day, preferably from about 100 to about 750 mg per day and more preferably from about 250-500 mg per day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing health professional.

The therapy may be repeated intermittently while symptoms are detectable or even when they are not detectable. The therapy may be provided alone or in combination with other drugs. In the case of Fas-related pathologies, the drugs that may be used in combination with the mimetics of the invention include, but are not limited to, anti-inflammatories, steroids and antimetabolites (for example, methotrexate).

Drugs used "in combination" are administered as part of a common method of treating a given pathology. Drugs used in combination may be administered in single or separate dosage forms. Separate dosage forms may be administered at the same or different times.

Toxicity:

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1).

EXAMPLES

The present invention is also described by means of the following examples. However, the use of these or other examples anywhere in the specification is illustrative only and in no way limits the scope and meaning of the invention or of any exemplified term. Likewise, the invention is not limited to any particular preferred embodiments described herein. Indeed, many modifications and variations of the invention may be apparent to those skilled in the art upon reading this specification and can be made without departing from its spirit and scope. The invention is therefore to be limited only by the terms of the appended claims along with the full scope of equivalents to which the claims are entitled.

Example 1

Molecular Model of a Fas Receptor Complex

Fas, a member of TNF superfamily, shares significant structural homology with the TNF receptor. The structure of the TNF receptor contains distinct "cystine-knot" repeating domains. (Naismith, J. H. et al. *Structure* 4, 1251-1262 (1996)). Loop structures in the first three domains as well as β-turns in proteins are considered to mediate roles in molecular recognition and binding. (Leszczynski, J. F. et al. *Science* 234, 849-855 (1986)). To develop a cystine-knot peptide mimetic, sites of protein-protein interaction that might be disrupted or influenced by small molecules were identified.

A molecular model of the Fas and FasL complex (FIG. 1*a*) was developed using the crystal structure of TNF receptor complex in our methodology as well as other already published models. (Watanabe-Fukunaga et al. supra; Naismith, J. H. et al. *J Biol Chem* 270, 13303-13307 (1995); Banner, D. W. et al. *Cell* 73, 431-445 (1993); Bajorath, J. *J Comput Aided Mol Des* 13, 409-418 (1999)). The overall features of the receptor-ligand interaction were noted to be very similar to that of TNF receptor ligand complex. See, U.S. Pat. No. 6,265,535. However, the ectodomain of the Fas receptor appears to be rotated about 10° compared to the transmembrane domain. Fas-FasL contact sites predicted by the molecular model are consistent with the mutation analysis data. (Beltinger, C. et al. *British Journal of Haematology* 102, 722-728 (1998)).

The Fas-FasL structural model suggested five surfaces where FasL can bind to Fas, designated Kp1, Kp2, Kp3, Kp4 and Kp7 (FIG. 1*b*), compared to such three sites identified in the TNF receptor (Takasaki et al. supra). The amino acids in the loops Kp1, 2, 3, 4 and 7 adopt well defined conformations (i.e., adopt statistically allowed conformations) as judged by Ramachandran plots (Ramachandran, G. N. et al. *Biopolymers* 6, 1255-1262 (1968); Ramachandran, G. N. et al. *Adv Protein Chem* 23, 283-438 (1968)) and profile analyses. (Zhang, K. Y. et al. *Protein Sci* 3, 687-695 (1994)).

Peptide analogs were designed from the various loop structures. Each mimetic was optimized for its ability to mimic the binding conformation of the loop and for its ring size which we have determined to be critical to reduce the inherent flexibility of mimetics. Specific features optimized included conformational mimicry between the loop structure and the mimetic, hydropathic value of the mimetics, dissociation rate (as measured from surface plasmon resonance; see., Example 3, infra), stability and solubility. A set of mimetics that were selected for biological assay is shown in Table 1.

TABLE 1

Exocyclic Mimetics Derived from Fas

| Fas Receptor Peptide | | | | Exocyclic Mimetic | | |
|---|---|---|---|---|---|---|
| Designation | | Sequence* | | Designation | | Sequence |
| Kp1 | 119 | CNSTVC | 124 (SEQ ID NO: 16) | Kp1-1 | YCNSTVCY | (SEQ ID NO: 10) |
| Kp2 | 77 | DKAHFSSKC | 85 (SEQ ID NO: 17) | Kp2-2 | YCDKAEHFCY | (SEQ ID NO: 11) |
| Kp3 | 103 | CTRTQ | 107 (SEQ ID NO: 18) | Kp3-2 | YCNTRTQNTCY | (SEQ ID NO: 12) |

TABLE 1-continued

Exocyclic Mimetics Derived from Fas

| Fas Receptor Peptide | | | Exocyclic Mimetic | | |
|---|---|---|---|---|---|
| Designation | Sequence* | | Designation | Sequence | |
| Kp4 | 69 CQEGKEY 75 | (SEQ ID NO: 19) | Kp4-2 | YCQEKEYCY | (SEQ ID NO: 13) |
| | | | Kp4-3 | YCQERKEYCY | (SEQ ID NO: 14) |
| Kp7 | 91 CDEGHGL 97 | (SEQ ID NO: 20) | Kp7-2 | YCDEGHLCY | (SEQ ID NO: 1) |
| | | | Kp7-3 | YCDEGLCY | (SEQ ID NO: 2) |
| | | | Kp7-4 | YCDEGYFCY | (SEQ ID NO: 3) |
| | | | Kp7-5 | YCDEGEYCY | (SEQ ID NO: 4) |
| | | | Kp7-6 | YCDEHFCY | (SEQ ID NO: 5) |
| | | | Kp7-7 | YCDEHGLCY | (SEQ ID NO: 6) |
| | | | Kp7-8 | YCDEHGQCY | (SEQ ID NO: 7) |
| | | | Kp7-9 | YCDEKFCY | (SEQ ID NO: 8) |
| | | | Kp7-10 | YCDEQFCY | (SEQ ID NO: 9) |

*Fas amino acid positions are obtained from the amino acid sequence of a full length Fas protein of sequence given in SEQ ID NO: 15.

Example 2

Inhibition of FasL Binding to Fas Receptor

Fas mimetic activity was evaluated in an assay that measured FasL-Flag binding (100 ng/ml) to Fas-Fc fusion protein immobilized onto plastic plates. The first generation mimetics Kp1-1, 2-2, 3-2, 4-2 and 7-2 were designed from different deduced binding sites of Fas to FasL and screened using a binding inhibition assay comprising 300 µM of peptide and 20 nM of soluble Fas receptor (FIG. 2A). The results indicated that Kp7 loop is a preferred surface for the design of mimetics as a template. Additional generations of exocyclic peptides derived from the Kp7 loop surface were also engineered. By the analysis of the interaction site between FasL and Fas, and biological activity of different mimetics, the aspartic and glutamic acids in Kp7 loop appear to represent the most relevant residues involved in the interaction. However, the particular acidic amino acid at each position is not critical. Hence, for example, either an aspartic acid or a glutamic acid residue can be present at either position. Modification of other residues of Kp7 led to some improvement of inhibitory activities as seen with the Kp7 series (FIG. 2A).

To compare the inhibitory activities of the Kp7 peptide series, dose-response studies were performed. The best activity was found with Kp7-6, which inhibited 50% of the FasL-Flag molecule binding to immobilized Fas-Fc at 150 μM (FIG. 2B).

Example 3

Binding Affinity and Specificity of Kp7 Mimetics

The kinetics of binding of Kp7-6, which mediated the best inhibitory activity to FasL, was performed using surface plasmon resonance (BIAcore™) analysis. FasL-Flag was immobilized onto a sensor chip and various solutions containing different concentrations of Kp7-6 were passed over the surface. FIG. 3A shows the sensogram result obtained with these different Kp7-6 concentrations. The $k_{on}$ and $k_{off}$ rate constants were estimated to be $6.85\times10^{1}\ M^{-1}s^{-1}$ and $7.65\times10^{-4}s^{-1}$, respectively, and a $K_D$ of value of $1.12\times10^{-5}$ M was obtained from the ratio of the dissociation/association rate constants. The $k_{off}$ value is considered as an important indicator in the development of therapeutics with biological activity (Benveniste, M. et al. *Br J Pharmacol* 104, 207-221 (1991); Yiallouros, I. et al. *Biochem J* 331, 375-379 (1998)), and generally correlates with potent biological effects. (Moosmayer, D. et al. *J Interferon Cytokine Res* 16, 471-477 (1996)). Although the $K_D$ of the Kp7-6-FasL interaction showed less affinity than that noted for Fas-FasL interactions (Starling, G. C. et al. *J Exp Med* 185, 1487-1492 (1997)), the $k_{off}$ rate was similar with usual antigen-antibody interaction, which suggests that Kp7-6 forms a stable receptor complex and may be useful practically. (Berezov, A. et al. *J Med Chem* 44, 2565-2574 (2001)).

To assess the specificity of Kp7-6 binding interaction, Fas, FasL and TNFα were immobilized on a sensor chip. Kp7-6 bound to FasL but not to TNFα, which indicates Kp7-6 bound to FasL specifically (FIG. 3B). Kp7-6 also bound to Fas (FIG. 3B). This observation is reminiscent of features of the soluble TNF receptor I (p55) which has been shown to form antiparallel homodimeric complexes in the absence of ligand. (Naismith, J. H. et al. *Structure* 4, 1251-1262 (1996)). These results suggest that Fas may also form such antiparallel dimers and the Kp7 loop may contribute to antiparallel dimer formation. No significant binding to TNF-R was detected.

Example 4

Inhibition of FasL-Induced Cytoxicity

To evaluate the effect of mimetics on Fas-mediated cytotoxicity, FasL-sensitive Jurkat cells were stimulated with soluble FasL-Flag fusion protein in the presence or absence of various concentrations of mimetics. The inhibitory effects of mimetics on Fas-mediated cytotoxicity were consistent with the results of the FasL-binding inhibition (FIG. 4). Kp7-6 showed a dose-dependent inhibitory activity. A concentration of 1 mM Kp7-6 protected more than 90% cells from Fas-mediated cytotoxicity (FIG. 4). Kp7-10 also showed a dose-dependent inhibition (FIG. 4). The cyclic peptides did not mediate any cytotoxicity for Jurkat cells in the range of concentration tested (data not shown). Large dose of Kp7-6 was used in this experiment for better signal-to-noise ratio. To determine if mimetics derived from other binding sites would potentially be able to interact synergistically to block the Kp7 surface, Kp7 was used in combination with mimetics. Neither Kp7-6 nor Kp7-10 used in combination with members of the Kp4 mimetics showed any significant synergy, suggesting that inhibition of the Kp7 binding site by itself is sufficient to antagonize FasL activity (data not shown).

Example 5

Inhibition of FasL-Induced Apoptosis

Figure 5:
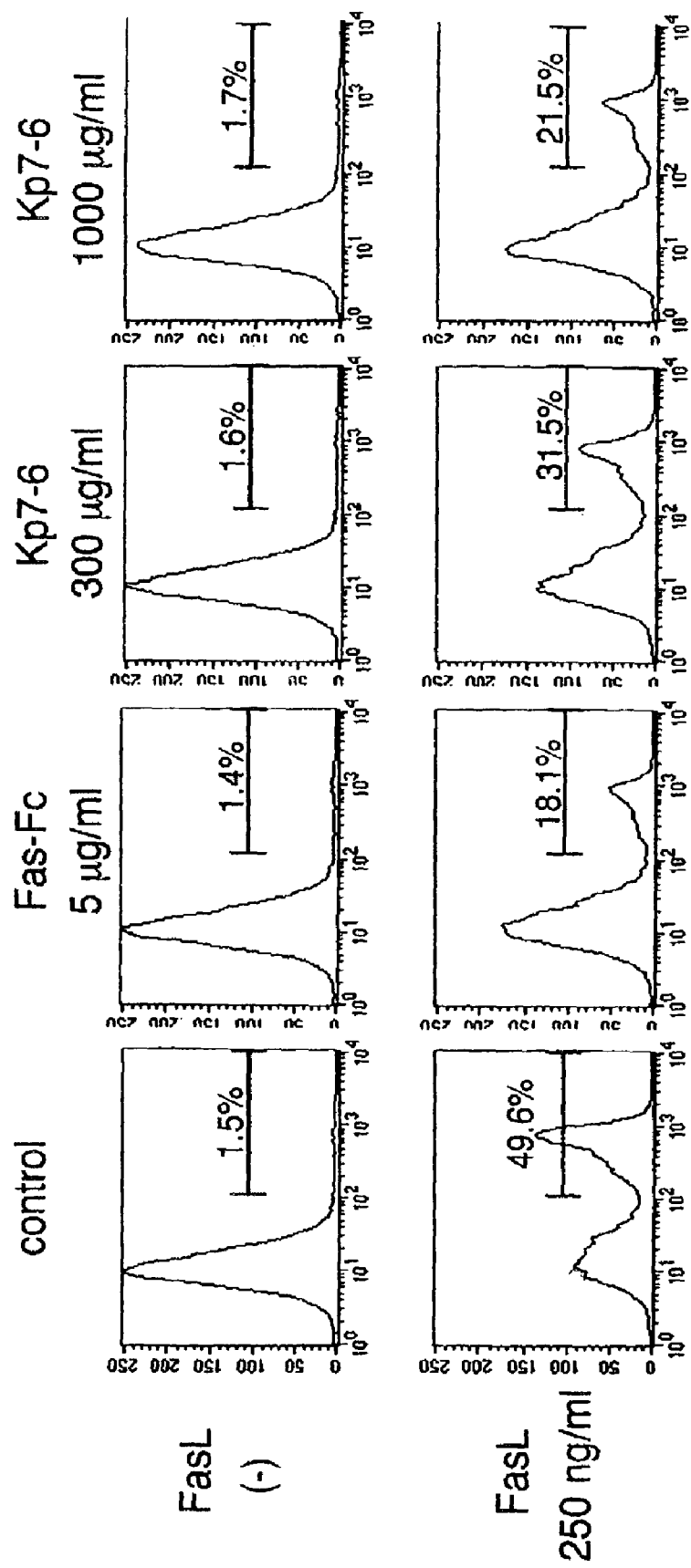
FIG. 5 depicts inhibition of FasL-induced apoptosis in Jurkat cells by the peptide mimetic Kp7-6. The number above the bar in each panel indicates the percentage of apoptotic (annexin-V$^+$) cells.

Biological activity of Fas mimetics was evaluated further by determining the effect of mimetics on Fas-L induced apoptosis. Apoptosis was measured by determining phosphatidylserine (PS) externalization on the cell membrane using annexin V. Translocation of PS to the outer leaflet of the plasma membrane is a common feature of apoptosis and is an early event that can be quantitatively measured using annexin V-FITC binding. Jurkat cells treated with FasL-Flag (200 ng/ml) for 3 h showed a marked increase in PS exposure compared with untreated cells (FIG. 5). The increase in Jurkat cell apoptosis was prevented by Kp7-6 in a dose-dependent manner (FIG. 5).

Example 6

Protection of Mice Against Con A-Induced Injury

Figure 6A:
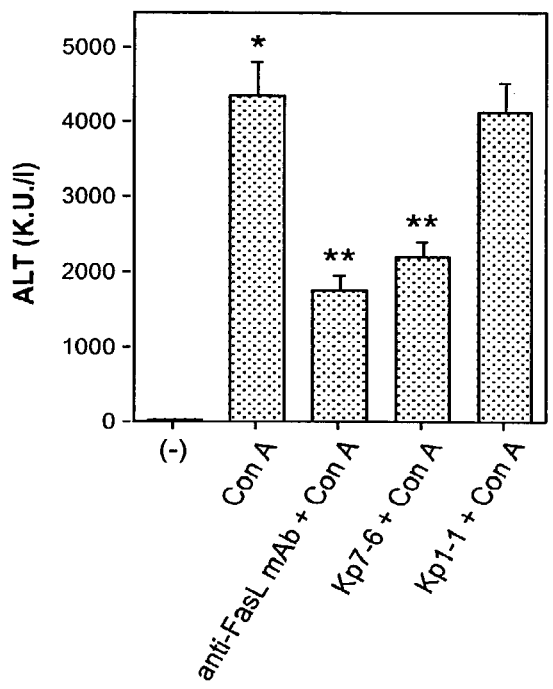
FIG. 6A-B illustrates results showing protection of mice against Con A induced liver injury by the antagonistic Fas mimetic peptide Kp7-7 as measured by serum activities of (A) alanine aminotransferase and (B) aspartate aminotransferase. *P<0.0001 versus control; **P<0.01 versus Con A-treated mice.
Figure 6B:
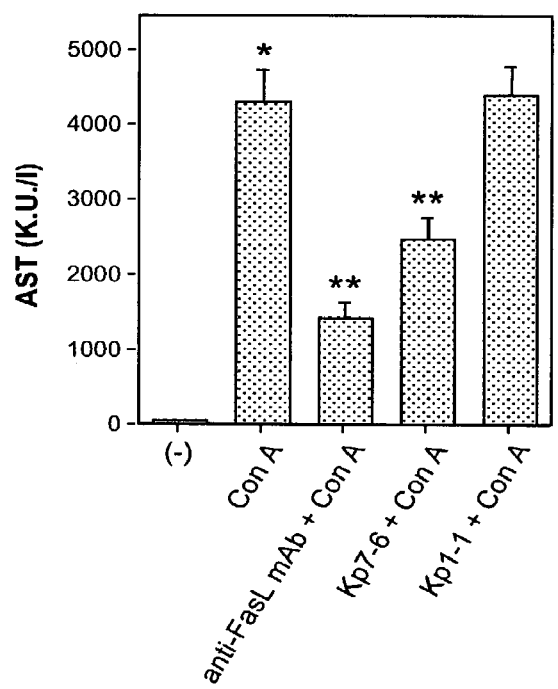

The biological activity of mimetic Kp7-6 was measured in vivo. FasL induced apoptosis is one of the primary and dominant pathways by which liver cells undergo apoptosis under various conditions such as viral infection, drug toxicity and other lesions. (Kakinuma, C. et al. *Toxicol Pathol* 27, 412-420 (1999); Famularo, G., et al. *Med Hypotheses* 53, 50-62 (1999); Gantner et al. supra). Several studies have found that blocking Fas signaling either by RNA interference or by oligonucleotides, will limit the extent of liver damage. (Zhang, H. et al. *Nat Biotechnol* 18, 862-867 (2000); Song, E. et al. *Nat Med* (2003)). The antagonistic effect of Kp7-6 in vivo was tested using the Con A-induced hepatitis model. C57BL/6 mice were pretreated intraperitoneally (IP) with anti-FasL monoclonal antibody, Fas mimetic peptides or saline. After 30 min, animals were challenged intravenously with Con A or saline. The induction of liver damage and inflammatory hepatitis was evaluated by measuring the serum activities of alanine aminotransferase (ALT) and aspartate aminotransferase (AST) 12 h after Con A treatment. The activities of both transaminases were reduced in Kp7-6 pretreated mice (FIG. 6A-B), indicating Kp7-6 blocked Fas-mediated hepatic injury in vivo. Kp1-1 did not block the hepatic injury (FIG. 6A-B). These results were consistent with in vitro data (shown in the preceding examples). Hence, a small rationally designed molecule that can effectively disable Fas receptor functions in vivo.

Suppression of the disease in anti-FasL monoclonal antibody pretreated mice was incomplete, consistent with genetic studies using Fas-deficient lpr/lpr mice, which also showed incomplete suppression of disease in the same Con A-induce hepatitis model. (Tagawa et al. supra). Mechanisms other than that mediated by the Fas-FasL system may also involved in this process.

Example 7

Fas Mimetic Inhibits Angiogenesis in the Eye

Fas Kp7 mimetic was used topically to treat angiogenesis in a mouse eye model. Angiogenesis was induced by placing pellets covered with fibroblast growth factor (FGF) that upon release in the eye lead to blood vessel growth. The degree of neo-vascularization was measured by the diffusion of FITC-dextran from newly formed/neovascularized blood vessels, using routine methods that are well known in the art. See, for example, De Fouw et al., *Microvasc. Res.* 38, 136-147 (1989); Tiedeken & Rovainer, *Microvasc. Res.* 41, 376-389 (1991); Rizzo et al., *Microvasc. Res.* 49, 49-63 (1995). Topical administration of the Fas Kp7 mimetic (1 mg/ml; 3 times/day for 7 days) led to virtual inhibition of new blood vessel formation. Control treatment with a TNF inhibitor also showed no effect.

Example 8

Fas Mimetic Agonist Activity in a Werner Syndrome Cell Line

Fas mimetic activity was further investigated in an assay that measured apoptosis of cells treated with Fas mimetics of the invention. Fas mimetic activity was investigated in two particular cells lines: N6803, an immortalized EBV-transformed human B-lymphoblastoid cell line (Kataoka et al., *Differentiation* 62, 203-211 (1997)), and WS10201, an EBV-transformed B-lymphoblastoid cell line derived from a Werner syndrome patient (see, Okada et al., *Biol. Pharm. Bull.* 21, 235-239 (1998); Hanma et al., *Mutat. Res.* 520, 15-24 (2002)). Werner syndrome is a recessive genetic disorder that causes premature aging and an enhanced risk of rare cancers (see, Goto et al., *Hum. Genet.* 105, 301-307 (1999)).

Live cells were separated by lymphocyte separation medium in cultured in wells of a 96-well plate ($10^5$ cells per well) for sixteen hours in the presence of an agonistic anti-Fas IgM antibody. Such antibodies are commercially available, e.g., from Beckman Coulter (Fullerton, Calif.). Cell were incubated either with anti-Fas IgM antibody alone or with the Fas mimetic Kp7-6 at doses of 10, 100 and 1000 ng/ml. A control group of cells was also incubated in culture medium alone (i.e., no anti-Fas IgM or Fas mimetic) under the same conditions. Apoptosis was assessed by TUNEL method (Gavrieli et al., *J Cell Biol* 119, 493-501 (1992); Gorczyca et al., *Cancer Res.* 53, 1945-1951 (1993); see, also, Ausubel et al. (Eds.) in *Current Protocols in Molecular Biology*, at page 14.13.15).

Figure 7A:
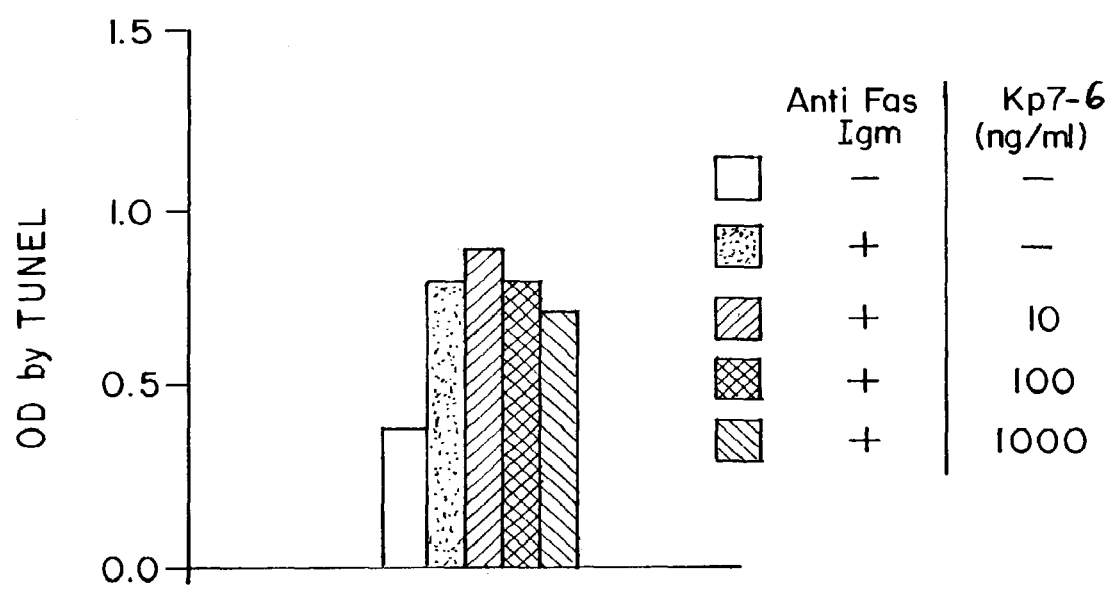
FIG. 7A-B shows apoptosis levels measured in (A) N6803 cells and (B) WS10201 cells treated with anti-Fas IgM antibody and Fas mimetic Kp7-6.
Figure 7B:
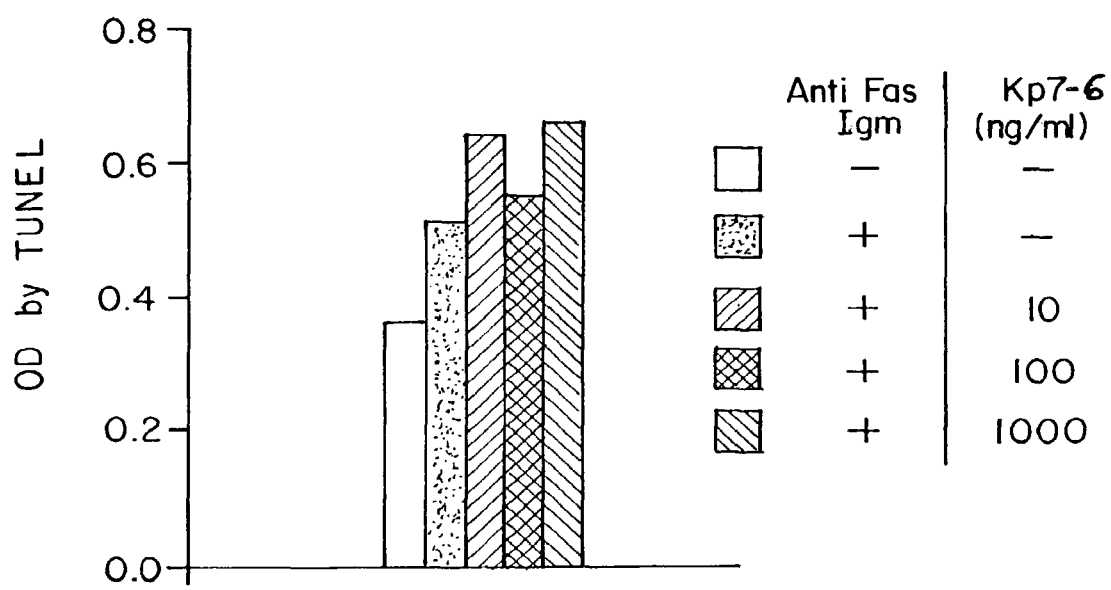

FIG. 7A-7B plots the apoptosis levels measured in N6803 and WS10201 cells, respectively. As expected, incubation of the cell lines with anti-Fas IgM increased apoptosis compared to cells incubated in medium along. Incubation with both anti-Fas IgM and Fas mimetic did not significantly alter apoptosis in the N6803 cell line compared to incubation with anti-Fas IgM along (FIG. 7A). However, Fas mimetic exhibited a synergistic effect with anti-Fas IgM in the WS10201 cell line, greatly enhancing apoptosis compared to treatment with anti-Fas IgM in the absence of Fas mimetic (FIG. 7B).

These data show that Fas mimetic of the invention can stimulate apoptosis in these circumstances, suggesting an agonistic effect in certain conditions. In particular, and without being limited by any particular theory or mechanism of action, receptors such as Fas are believed to exists in two states (see, Lef, *Trends Pharmacol. Sci.* 16, 89-97 (1995)): an inactive monomer form and an active, signal competent dimer. At low concentrations, such as the concentrations used in these experiments, Fas mimetic is believed to bind to the signal competent dimer form of Fas but does not shift the receptor population to the inactive monomer state. In these conditions, particularly in the absence of FasL, Fas mimetics of the invention are expected to exhibit at least a transient stimulation of Fas activity and so have an agonistic effect. At higher concentrations, however, Fas mimetics are believed to shift equilibrium of Fas to the signal incompetent monomer form, thereby inhibiting Fas signal and so having an antagonistic effect. Such "inverse agonist" properties are known in the art and have been described for peptide mimetics of other receptors, such as the CD4 receptor. See, for example, Horie et al., *Exp. Mol. Pathol.* 73, 93-103 (2002).

Example 9

Experimental Protocols

Materials. Human recombinant TNFα was obtained from Roche Diagnostics (Indianapolis, Ind.). Flag-tagged soluble human Fas ligand (FasL-Flag) and human Fas extra cellular domain-IgGFc fusion protein (Fas-Fc) were purchased from Kamiya Biomedical (Seattle, Wash.). Human recombinant TNF-receptor (I) extracellular domain-IgGFc fusion protein (TNFRI-Fc) was obtained from R & D systems (Minneapolis, Minn.). Anti-Flag-HRP antibody, hydrogen peroxide solution, 3,3',5,5'-tetramethylbenzidine (TMBZ) and concanavalin A were from Sigma Biochemical Co. (St. Louis, Mo.).

Cell lines. American Type Culture Collection Jurkat cells were grown in RPMI 1640 medium supplemented with 10% heat inactivated fetal calf serum, L-glutamine (2 mM), penicillin (100 U/ml) and streptomycin (100 µg/ml) at 37° C. in a humidified 5% CO2 atmosphere.

Mice. Eight-week-old C57BL/6 (B6) mice were purchased from CLEA JAPAN Inc. (Tokyo, Japan). All mice used were maintained under specific pathogen-free conditions in our animal facility.

Molecular Modeling. Computer modeling and the structural analysis were performed using both QUANTA and INSIGHT (Molecular Simulation, San Diego, Calif.). The model peptides designed were constructed from their sequences and folding using CHARMM. The side chain of amino acid residues were first positioned to permitted conformation using the Ponders rotamer (Ponder, J. W. et al. *J Mol Biol* 193, 775-791 (1987)) database provided in QUANTA. Then the folded peptides were minimized to convergence with a dielectric constant set to 80. The molecular model of the human Fas/FasL complex was built by using Modeller 3.0 (Sali, A. et al. *J Mol Biol* 212, 403-428 (1990); Sali, A. et al. *Trends in Biochem Sci* 15, 235-240 (1990)) using the crystal structure of TNF receptor and molecular model of Fas (Bajorath supra) from Brookhaven database. (Bernstein, F. C. et al. *J Mol Biol* 112, 535-542 (1977)). The conformation of loops were constructed using both loop search algorithm and CONGEN. (Bruccoleri, R. E. et al. *Nature* 335, 564-568 (1988)). The quality of the model were assessed using Ramachandran plot (for phi, psi violations) and profile analysis. (Zhang et al. supra). The Fas/FasL complex was optimized using rigid body minimization using XPLOR 3.1 (Brünger, A. T. X-PLOR. Version 3.1. A System for X-ray Crystallography and NMR. (Yale University Press, New Haven, Conn., 1992)) and INSIGHT.

Mimetics were designed from essential sequences of Fas-FasL interactions. About five to seven amino acid sequences of Fas, have been used to mimic the conformation of loops Kp1 to Kp7 as shown in Table 1.

Peptide synthesis and cyclization. Peptides were synthesized by solid-phase methods, deprotected, and released from the resin using anhydrous HF. Peptides were lyophilized and further purified by HPLC utilizing a C18 column and then relyophilized. Peptides were more than 95% pure by HPLC analysis and mass spectrometry.

The peptides containing internal cysteine residues were refolded and oxidized as described previously. (Takasaki et al. supra). Briefly, peptides were dissolved at 100 µg/ml in distilled water adjusted to pH 8.0 by $(NH_4)_2CO_3$ and stirred at 4° C. until 95% formation of intramolecular disulfide bonds had been confirmed by DTNB (Sigma Biochemical Co., St. Louis, Mo.). The cyclized peptides were lyophilized and analyzed for purity by HPLC. These peptides showed greater than 90% purity by HPLC analysis.

Solid phase ligand binding assay. Fas-Fc fusion protein (250 ng/ml) diluted in PBS was immobilized onto 96 well ELISA plate (Costar, High Wycombe, UK) by incubating overnight at 4° C. After blocking with PBS containing 1% skim milk overnight at 4° C. and subsequent washing with PBS containing 0.05% Tween 20 (PBS-Tw), Flag-tagged soluble FasL (100 ng/ml)/peptide solution preincubated in PBS containing 1% skim milk for 1 h at 37° C. was added onto the Fas-Fc coated wells. After 2 h incubation at room temperature, the plate was washed with PBS-Tw, and anti-FLAG (M2)-HRP antibody 1:2500 in PBS containing 1% skim milk was added. After 1 h incubation at room temperature, the plate was washed with PBS-Tw, and the enzyme reaction was started by adding the substrate solution (0.1 M sodium acetate buffer (pH 5.0) containing 100 µg/ml of TMBZ and 0.005% (v/v) $H_2O_2$) and stopped with 2N $H_2SO_4$. The absorbance at 450 nm was measured with an ELISA reader.

Biosensor analysis. All experiments were carried out on a BIAcore 3000 instrument (Biacore A G, Uppsala, Sweden) at 25° C. using PBS, pH 7.4, containing 0.005% surfactant P20 (Biacore AG) as the running buffer. FasL-Flag, Fas-Fc or TNFRI-Fc was immobilized on research-grade CM5 sensor chips (Biacore AG) using standard N-ethyl-N-dimethylaminopropyl carbodiimide/N-hydroxysuccinimide coupling. Immobilization was performed in 10 mM sodium acetate buffer at pH 4.5 for FasL-Flag and Fas-Fc, and at pH 4.0 for TNFRI-Fc. After coupling, excess N-hydroxysuccinimide groups were inactivated with ethanolamine. For binding studies, about 1500 resonance units (RU) of FasL-Flag, Fas-Fc and TNFRI-Fc were coupled to the chips. Surface plasmon resonance (SPR) measurements were carried out at a flow rate of 20 ml min$^{-1}$. Data were analyzed with the BIA evaluation 3.0 software (Biacore AG). The sensograms give values for the relative response in resonance units (RU) after background subtraction versus time in seconds. The association phase injection time was 300 seconds followed by dissociation buffer.

Cytotoxicity assay. Twenty microliters of Jurkat cells at $1\times10^5$ cells/ml were plated in 96-well U-bottom plates. FasL-Flag (120 ng/ml in culture medium) was preincubated with equal volume of peptide sample in PBS for 1 h at 37° C., and 20 µl of mixture was added to each well. After an incubation period of 24 h, each culture was pulsed with 1 µCi of [$^3$H]-thymidine for 24 h before harvesting on glass fiber filters. Incorporation of the $^3$H-thymidine obtained with culture medium alone and with 30 ng/ml of FasL was used as reference for 100% survival and 0% survival, respectively. Survival (%) by several doses of peptides was plotted. Incorporation of the radioactive label was measured by liquid scintillation counting (Wallac, Finland) and expressed as the arithmetic mean counts per minute (cpm) of triplicate cultures.

Flow cytometry assay for apoptosis. Apoptotic cells were detected by annexin V-FITC binding to phosphatidylserine (PS) expressed on the cell membrane in the early phase of apoptosis using a commercial kit purchased from Roche (Indianapolis, Ind.). Briefly, $1\times10^5$ Jurkat cells were cultured with FasL-Flag (250 ng/ml) in the presence or absence of peptide sample for 3 h. The cells were then washed with PBS and resuspended in 100 µl of binding buffer containing optimal concentration of calcium, FITC-conjugated annexin V and propidium iodide (PI) for 10 min. at room temperature. After adding an additional 400 µl of binding buffer, cells were analyzed by FACScan (Becton Dickinson Immunocytometry Systems, San Jose, Calif.). CELLQuest software programs (Becton Dickinson Immunocytometry Systems, San Jose, Calif.) were used for collecting and analyzing data. Early apoptotic cells were expressed as percentage of cells positive for annexin V and negative for PI. 10,000 cells were analyzed in each condition.

Administration of Con A and measurement of serum transaminase activity. Hepatic damage was induced by injection of a single dose of 0.5 mg Con A dissolved in pyrogen-free saline and administered to mice via the tail vein. Anti-FasL monoclonal antibody (MFL-4; Kayagaki, N. et al. *Proc Natl Acad Sci USA* 94, 3914-3919 (1997)) or Fas mimetic peptide (Kp7-6 or Kp1-1) was diluted with pyrogen-free saline and injected in a single dose intraperitoneally 30 minutes before Con A.

Blood samples were collected from mice at 12 h after Con A injection, and the serum was taken by centrifugation. Serum activities of alanine aminotransferase (ALT) and aspartate aminotransferase (AST) were measured by Lippi-Guidi's method (Iatrozyme TA-LQ: Dia-Iatron Inc., Tokyo, Japan). (Lippi, U. et al. *Clin Chim Acta* 28, 431-437 (1970)).

Statistical analysis. Results are expressed as mean USE, and analyzed by the Student's t test or analysis of variance (ANOVA) where appropriate. Post hoc comparisons were performed using Scheffe test. A 95% confidence interval was used to define statistical significance.

REFERENCES CITED

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed is:

1. A Fas mimetic represented by the formula (I)

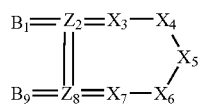

wherein $B_1$ and $B_9$ are independently a peptide of 1-6 genetically encoded amino acids, at least one of which is a genetically encoded hydrophobic amino acid, or a genetically encoded aromatic amino acid, $Z_2$ is cysteine, that forms a covalent linkage with $B_1$, $X_3$ or $X_4$ and $Z_8$, $Z_8$ is cysteine, that forms a covalent linkage with $B_9$, $X_7$ and $Z_2$, $X_3$ is a genetically encoded hydrophilic amino acid or null, $X_4$ is aspartic acid or glutamic acid, $X_5$ is aspartic acid or glutamic acid, $X_6$ is selected from the group consisting of histidine, lysine, arginine, asparagine or glutamine, $X_7$ is a genetically encoded aromatic amino acid "—" is a covalent linkage comprising an amide or a substituted amide thereof, and "═" is a covalent linkage, or a pharmaceutically acceptable salt.

2. The mimetic of claim 1 wherein $X_3$ is null.

3. The mimetic of claim 2 wherein $X_4$ is aspartic acid and $X_5$ is glutamic acid.

4. The mimetic of claim 3 wherein $X_7$ is phenylalanine.

5. The mimetic of claim 4 wherein $B_1$ or $B_9$ is a genetically encoded aromatic amino acid.

6. The mimetic of claim 5 wherein each of $B_1$ and $B_9$ is a genetically encoded aromatic amino acid.

7. The mimetic of claim 5 wherein $B_1$ or $B_9$ is tyrosine.

8. The mimetic of claim 7 wherein each of $B_1$ and $B_9$ is tyrosine.

9. The mimetic of claim 1 wherein said mimetic has a $K_D$ for FasL of $10^{-4}$ M or less.

10. The mimetic of claim 9 wherein said mimetic has a $K_D$ for FasL of $10^{-5}$ M or less.

11. The mimetic of claim 1 wherein said mimetic has a $k_{off}$ for FasL of $10^{-3}$ s$^{-1}$ or less.

12. The mimetic of claim 1 wherein said mimetic has a $k_{off}$ for FasL of $10^{-4}$ s$^{-1}$ or less.

13. A pharmaceutical composition comprising a mimetic of claim 1 and a pharmaceutically acceptable excipient.

14. The pharmaceutical composition of claim 13 wherein said excipient is a member selected from the group consisting of a diluent, buffer, carrier, stabilizer and preservative.

* * * * *